(12) United States Patent
Morita

(10) Patent No.: US 9,212,132 B2
(45) Date of Patent: Dec. 15, 2015

(54) (METH)ACRYLIC ACID ESTER, ACTIVATION ENERGY RAY CURING COMPOSITION, AND INKJET RECORDING INK

(71) Applicant: Mitsunobu Morita, Shizuoka (JP)

(72) Inventor: Mitsunobu Morita, Shizuoka (JP)

(73) Assignee: Ricoh Company Ltd., Tokyo (JP)

( * ) Notice: Subject to any disclaimer, the term of this patent is extended or adjusted under 35 U.S.C. 154(b) by 0 days.

(21) Appl. No.: 13/687,224

(22) Filed: Nov. 28, 2012

(65) Prior Publication Data

US 2013/0144057 A1  Jun. 6, 2013

(30) Foreign Application Priority Data

Dec. 5, 2011  (JP) .................................. 2011-266160
May 14, 2012  (JP) .................................. 2012-110837

(51) Int. Cl.
| | | |
|---|---|---|
| *C07D 211/00* | (2006.01) | |
| *C07C 271/12* | (2006.01) | |
| *C07D 295/185* | (2006.01) | |
| *C07C 271/14* | (2006.01) | |
| *C07D 211/46* | (2006.01) | |
| *C09D 11/101* | (2014.01) | |
| *C09D 11/30* | (2014.01) | |

(52) U.S. Cl.
CPC ............. *C07C 271/12* (2013.01); *C07C 271/14* (2013.01); *C07D 211/46* (2013.01); *C07D 295/185* (2013.01); *C09D 11/101* (2013.01); *C09D 11/30* (2013.01)

(58) Field of Classification Search
CPC .. C07D 211/46; C07D 211/74; C07D 211/94; G03F 7/028; G03F 7/031; G03F 7/033
See application file for complete search history.

(56) References Cited

U.S. PATENT DOCUMENTS

| | | | |
|---|---|---|---|
| 4,126,747 A | 11/1978 | Cowherd, III et al. | |
| 4,161,596 A | 7/1979 | Cowherd, III et al. | |
| 5,030,726 A | 7/1991 | Noriyuki et al. | |
| 6,117,921 A | 9/2000 | Ma et al. | |
| 6,180,560 B1 | 1/2001 | Hayakawa et al. | |
| 6,409,328 B1* | 6/2002 | Ohkawa ........................ 347/100 |
| 2003/0205171 A1 | 11/2003 | Adams et al. | |
| 2004/0071187 A1 | 4/2004 | Hayakawa et al. | |
| 2005/0256058 A1 | 11/2005 | Powers et al. | |
| 2007/0115327 A1 | 5/2007 | Nakamura | |
| 2009/0155484 A1 | 6/2009 | Nakamura et al. | |
| 2009/0286848 A1 | 11/2009 | Wong et al. | |
| 2010/0151388 A1* | 6/2010 | Yang et al. .................. 430/285.1 |
| 2011/0033803 A1* | 2/2011 | Hatakeyama et al. ..... 430/285.1 |
| 2011/0092610 A1 | 4/2011 | Habashi et al. | |

FOREIGN PATENT DOCUMENTS

| | | |
|---|---|---|
| CN | 101503378 A | 8/2009 |
| EP | 0 376 751 A1 | 7/1990 |
| GB | 1 564 453 | 4/1980 |
| JP | 62-285959 | 12/1987 |
| JP | 63-054416 | 3/1988 |
| JP | 10-087768 | 4/1998 |
| JP | 10-095158 | 4/1998 |
| JP | 2000-154169 | 6/2000 |
| JP | 2003-012744 | 1/2003 |
| JP | 2005-524751 | 8/2005 |
| JP | 2006-123459 | 5/2006 |
| JP | 2006-257155 | 9/2006 |
| JP | 2007-138118 | 6/2007 |
| JP | 2007-177174 | 7/2007 |
| JP | 2007-231231 | 9/2007 |
| JP | 2007-231233 | 9/2007 |
| JP | 2007-526254 | 9/2007 |
| JP | 2009-067926 | 4/2009 |
| JP | 2009-144057 | 7/2009 |
| JP | 2009-179681 | 8/2009 |
| JP | 2009-249561 | 10/2009 |
| JP | 2010-013506 | 1/2010 |
| JP | 2010-058405 | 3/2010 |
| JP | 2010-069623 | 4/2010 |
| JP | 2010-181677 | 8/2010 |
| JP | 2011-519966 | 7/2011 |
| JP | 2012-025862 | 2/2012 |

(Continued)

OTHER PUBLICATIONS

Lawson, JK. et. al. Dimethylamides from Alkali Carboxylates and Dimethylcarbamoyl Chloride. J. Org. Chem. 1963, vol. 28, p. 234.*

(Continued)

*Primary Examiner* — Janet L Andres
*Assistant Examiner* — Ben S Michelson
(74) *Attorney, Agent, or Firm* — Oblon, McClelland, Maier & Neustadt, L.L.P.

(57) ABSTRACT

(Meth)acrylic acid ester, which contains one or more partial structures each represented by the following formula 1 in a molecule thereof, wherein the partial structure is a urethane structure which does not have a hydrogen atom directly bonded to a nitrogen atom of the following formula 1:

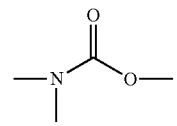

Formula 1 where the nitrogen atom is not bonded to a hydrogen atom.

4 Claims, No Drawings

(56) References Cited

FOREIGN PATENT DOCUMENTS

| JP | 2012-180503 | 9/2012 | |
|---|---|---|---|
| KR | 10-2007-0015665 | 2/2007 | |
| WO | WO 2009/087177 | A1 * | 7/2009 |
| WO | WO 2009087177 | A1 * | 7/2009 |

OTHER PUBLICATIONS

Frei, RW. et al. Fluorigenic Labeling of N-methyl- and N,N-dimethylcarbamates with 4-chloro-7-nitrobenzo-2,1,3-oxdiazole. Analytical Chemistry. 1972, vol. 44, p. 2046.*
Carey, FA. Organic Chemistry 6th Ed. McGraw Hill. 2006, chapter 1, p. 9.*
Honda, T. et al. Novel stereoselective synthesis of enantiopure (+)-N-Boc-norpandamarilactonine-A, the intermediate for pandamarilactonines. Tetrahedron Letters. 2006, vol. 47, p. 6253.*
Ghosh, AK. et al. Ring-Closing Metathesis Strategy to Unsaturated γ- and δ-lactones: Synthesis of Hydroxyethylene Isostere for Protease Inhibitors. Tetrahedron Letters. 1998, vol. 39, p. 4653.*
Bowman, CN. et al. Development of highly reactive mono-(meth)acrylates as reactive diluents for dimethacrylate-based dental resin systems. Biomaterials. 2005, vol. 26, p. 1330.*
Nie, J. et al. Synthesis and Photopolymerization of 2-(Acryloyloxy)ethyl Piperidine-1-Carboxylate and 2-(Acryloyloxy)ethyl Morpholone-4-Carboxylate. Journal of Applied Polymer Science. 2011, vol. 119, p. 1980.*
Optical Applied Technologies and Materials Dictionary, Chapter 2 Section 2, edited by the editorial committee of Optical Applied Technologies and Materials Dictionary, Kabushikigaisha Sangyo Gijutsu Service center, published in 2006.
The latest/ Optimization of UV cured resin, Chapter 1, Technical Information Institute Co., Ltd., published in 2008.
Extended Search Report issued Mar. 15, 2013 in European Application No. 12195618.9.
Joachim Probst, et al., "Homo-and Copolymerization of N,N-disubstituted carbamoyloxyalkyl acrylates and methacrylates", Makromol. Chem., vol. 177, No. 9, 1976, pp. 2681-2695.
Peter Molz, et al., "Synthesis and first in vitro cytotoxicity studies of bis(2-chloroethyl) amino group containing polymers. Pharmacologically active polymers: 22", Int. J. Biol. Macromol., vol. 2, No. 4, 1980, pp. 245-250.
V. V. Mikheev, et al., "Synthesis of urethane alcohol methacrylates", retrieved from STN Database accession No. 1988:610502, 1988. 1 page.
Paolo Ferruti, et al., "PHEMA Hydrogels Obtained by a Novel Low-Heat Curing Procedure with a Potential for In Situ Preparation", Macromolecular Bioscience, vol. 4, No. 6, 2004, pp. 591-600.
Zhen-Feng Li, et al. "Photopolymerization Kinetics of 2-(acryloyloxy)ethyl Pyrrolidine-1-carboxylate", retrieved from STN Database accession No. 2008:682059, 2008, 1 page.
Jens Voepel, et al., "Alkenyl-Functionalized Precursors for Renewable Hydrogels Design", Journal of Polymer Science Part A: Polymer Chemistry, XP-002692890, 2009, p. 3597, pp. 3595-3606.
Ming Xiao, et al., "Synthesis and Photopolymerization of 2-(Acryloyloxy)ethyl Piperidine-1-Carboxylate and 2-(Acryloxy)ethyl Morpholone-4-Carboxylate", Journal of Applied Polymer Science, vol. 119, No. 4, 2011, pp. 1978-1985.
Antonio L. Medina-Castillo, et al., "Novel Synthetic Route for Covalent Coupling of Biomolecules on Super-Paramagnetic Hybrid Nanoparticles", Journal of Polymer Science, Part A, Polymer Chemistry, vol. 50, No. 19, 2012, pp. 3944-3953.

* cited by examiner

(METH)ACRYLIC ACID ESTER, ACTIVATION ENERGY RAY CURING COMPOSITION, AND INKJET RECORDING INK

BACKGROUND OF THE INVENTION

1. Field of the Invention

The present invention relates to novel (meth)acrylic acid ester, and an activation energy ray curing composition using the same, and an inkjet recording ink using the same.

2. Description of the Related Art

As a method for forming an image on a recording medium, such as paper, there are various methods, such as electrophotography, sublimation recording, thermal transfer recording, and inkjet recording. Among them, the inkjet recording has high efficiency in ink consumption, and therefore is excellent in resources saving, and can keep an ink cost per unit recording low. However, there are various problems when an aqueous ink is used. There are inks using organic solvent instead of water, but these inks also have different problems.

Because of the reasons as mentioned, attentions have recently been attracted to inkjet recording using an activation energy ray-curing ink. The activation energy ray-curing ink has been described as a UV ray-curing ink composition in various literatures, and documents. Typically, the activation energy ray-curing ink contains a polymerization initiator and monomers as essential components, and optionally contains substances such as a pigment, oligomers, polymers, and a sensitizing agent (Optical Applied Technologies and Materials Dictionary (edited by the editorial committee of Optical Applied Technologies and Materials Dictionary, Kabushikigaisha Sangyo Gijutsu Service center, published in 2006); The latest/Optimization of UV cured resin (Technical Information Institute Co., Ltd., published in 2008) etc.).

As the monomer component, a plurality of monomers are used in view of curing speed (sensitivity), viscosity of an ink, and properties of a film after curing. It is common that a low molecular weight monomer that has a molecular weight of 700 or smaller, has low viscosity, and is excellent in reactivity, and a polyfunctional high molecular weight monomer are used in combination. Since the monomers are a main component constituting about 80% by mass of the inkjet recording ink, a research on a formulation (combination) thereof has been actively conducted as well as a development of a material thereof.

For example, disclosed are an invention using an ester or amide compound of tri- or higher functional (meth)acrylic acid having an alkylene oxide group in a molecule thereof (Japanese Patent Application Laid-Open (JP-A) No. 2007-231231), an invention using a combination of an ester or amide of tri- or higher functional (meth)acrylic acid having an alkylene oxide group in a molecule thereof and an ester or amide of monofunctional (meth)acrylic acid having C6-C12 alkyl site (JP-A No. 2007-231233), an invention using a combination of an aliphatic (meth)acrylate compound containing a secondary hydroxyl group and a compound containing a nitrogen atom and a polymerizable unsaturated bond in a molecule thereof (JP-A No. 2009-67926), and an invention using a polymerizable compound containing a polymerizable unsaturated bond and an amino group in a molecule thereof (JP-A No. 2009-144057).

Moreover, use of a monomer compound having a urethane structure has been proposed, and examples thereof include an invention including urethane acrylate oligomers (JP-A Nos. 2006-257155, and 2009-249561). However, these urethane acrylate oligomers have the NH structure of a hydrogen bond, and have high molecular weights, and therefore have high viscosity. Accordingly, the urethane acrylate oligomer is not suitable for use in an inkjet recording ink, and it is used as a mixture with another (meth)acrylic acid monomer of low viscosity.

As for a low molecular weight (meth)acrylic acid monomer having a urethane structure and having a molecular weight of 700 or smaller, disclosed is an ink for color filter, which uses a methacrylic acid monomer having a urethane structure including an NH structure (JP-A No. 2010-181677), but it is also not suitable for an inkjet recording ink because the viscosity thereof is high.

Meanwhile, urethane (meth)acrylate or urethane (meth)acrylate oligomers having an NH structure have been used in various activation energy ray-curing compositions (JP-A Nos. 62-285959 and 63-054416) other than inkjet recording inks. However, these also increase the viscosity thereof, and therefore there is a restriction due to the viscosity depending on intended use thereof, or it is necessary to use in combination with a monomer of low viscosity.

Further, for the purpose of improving properties such as high curing ability, flexibility of a cured film, solvent resistance and adhesion with a base material, proposed are an invention using a monomer having an alicyclic structure (JP-A No. 2007-138118), an invention using a monomer having a heterocyclic structure such as dioxolane and dioxane (JP-A No. 2007-177174), and an invention using a plurality of monomers each having two or more alicyclic structures, heterocyclic structures, or aromatic ring structures (JP-A No. 2009-179681).

However, these monomer compounds tend to be evaporated, and therefore they cause discomfort due to odor distinctive to the monomers. Moreover, there is a problem that an alicyclic ring or aromatic ring in the structure does not give sufficient adhesion.

SUMMARY OF THE INVENTION

When the conventional monomer is used in an ink, the odor thereof is an important issue. Generally, a large amount of a low molecular weight reactive monomer having a molecular weight of 700 or smaller, which is called a diluent, is formulated also as a solvent to various activation energy ray-curing inks to appropriately maintain properties of the inks, such as viscosity. However, these low molecular weight monomer compounds have distinct odor, which tends to give discomfort.

Odor of a chemical compound is recognized by human by detecting molecules of the compounds scattered in the air with sense of smell. Therefore, it is important for the monomer compound having distinct odor that the compound itself is difficult to be scattered in the air. Therefore, one of methods for improving odor of an ink is, for example increasing a molecular weight of a monomer compound, or increasing intermolecular interaction by introducing a polar functional group to thereby inhibit scattering of the monomer compound.

However, when an ink is produced only with monomer compounds having high molecular weights, a resultant has high viscosity, which is not suitable for use that requires low viscosity, such as an inkjet recording ink. Moreover, the low molecular weight monomer compounds disclosed in the aforementioned related art are also not insufficient in improving a problem of odor.

Accordingly, it is an object of the present invention to provide (meth)acrylic acid ester, which is excellent in photopolymerization reactivity and curing ability with activation energy rays and whose odor is improved.

The present inventors have diligently conducted researches to achieve the aforementioned object. As a result, they have found that discomfort odor that is distinctive to a monomer is reduced and reactivity and curing ability to activation energy rays are excellent by introducing a certain functional group into a molecular structure of a (meth)acrylic acid ester compound that is an activation energy ray-curing monomer contained in an activation energy ray curing composition and in an ink. Based upon this insights, the present invention has been accomplished.

The present invention has accomplished based upon the insights of the present inventors, and means for solving the aforementioned problems are as follows:

(Meth)acrylic acid ester of the present invention contains: one or more partial structures each represented by the following formula 1 in a molecule thereof, wherein the partial structure is a urethane structure which does not have a hydrogen atom directly bonded to a nitrogen atom of the following formula 1:

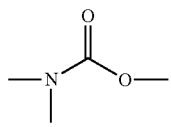

Formula 1 where the nitrogen atom is not bonded to a hydrogen atom.

The present invention can solve the various problems in the art, can achieve the aforementioned object, and can provide (meth)acrylic acid ester, which is excellent in photopolymerization reactivity and curing ability with activation energy rays and whose odor is improved.

DETAILED DESCRIPTION OF THE INVENTION

(Meth)Acrylic Acid Ester

The present invention will be specifically explained hereinafter.

The (meth)acrylic acid ester of the present invention contains one or more partial structures each represented by the following formula 1 in a molecule thereof, wherein the partial structure is a urethane structure which does not have a hydrogen atom directly bonded to a nitrogen atom of the following formula 1:

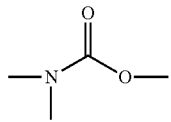

Formula 1

In the formula 1, the nitrogen atom is not bonded to a hydrogen atom.

The (meth)acrylic acid ester of the present invention can be cured (dried) upon application of activation energy rays. Moreover, the (meth)acrylic acid ester of the present invention can be used to produce an activation energy ray curing composition, which can be used for printing inks, various adhesives, and coating agents.

The printing ink can be suitably applied in various printing use such as offset printing and screen printing. Among them, the (meth)acrylic acid ester is suitable for an inkjet recording ink (may be referred to as an "ink") that needs to be low viscosity, and an inkjet recording method using such ink.

The (meth)acrylic acid ester is appropriately selected depending on the intended purpose without any limitation, provided that it contains at least one partial structure represented in the formula 1 in a molecular thereof. Preferable embodiments thereof include those having the structures represented by the following formulae 2 to 6:

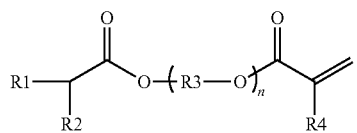

Formula 2

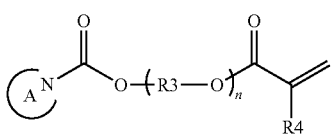

Formula 3

In the formulae 2 and 3, R1 and R2 may be identical or different, and each represent an alkyl group or an alkyl group containing a hetero atom, R3 represents a C1-C15 bivalent group or a C1-C15 bivalent group having a hetero atom, n represents an integer of 1 to 4, R4 represents a hydrogen atom or a methyl group, and A represents a ring structure containing at least one nitrogen atom.

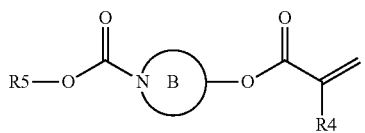

Formula 4

In the formula 4, R4 represents a hydrogen atom or a methyl group, R5 represents an alkyl group or an alkyl group containing a hetero atom, and B represents a ring structure containing at least one nitrogen atom.

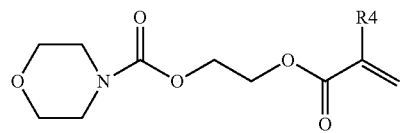

Formula 5

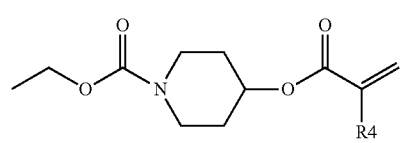

Formula 6

In the formulae 5 and 6, R4 represents a hydrogen atom or a methyl group.

R1 and R2 of the formula 2 each represent an alkyl group or an alkyl group containing a hetero atom, preferably an alkyl group.

The ring structure A of the formula 3 is a ring structure formed by bonding R1 with R2, and various ring structures can be introduced thereto. Among them, a morpholine ring and a piperidine ring are preferable. As for the (meth)acrylic acid ester having a morpholine ring, one having the structure represented by the formula 5 is preferable.

R3 of the formulae 2 and 3 is a C1-C15 bivalent group or a C1-C15 bivalent group containing a hetero atom, which may be of a linear chain, or branched chain, and is preferably an alkylene group, more preferably an ethylene group.

R5 of the formula 4 represents an alkyl group or an alkyl group containing a hetero atom, but it is preferably an alkyl group. Similarly to the ring structure A, various ring structures can be introduced to the ring structure B. Among them, a piperidine ring is preferable. As for the (meth)acrylic acid ester having a piperidine ring, one having the structure represented by the formula 6 is preferable.

Further, the (meth)acrylic acid ester preferably contains two or more partial structures each represented by the formula 1 in a molecule thereof, and examples of such (meth)acrylic acid ester include those represented by the following formulae 7, 10, and 11:

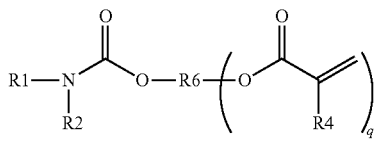

Formula 7

In the formula 7, R1 and R2 may be identical or different and each represents an alkyl group or an alkyl group containing a hetero atom, R6 represents a C1-C15 tri- or higher valent group or a C1-C15 tri- or higher valent group containing a hetero atom, q represents 2 or 3, and R4 represents a hydrogen atom or a methyl group, in which R1 and R2 may form a ring structure bonded via a carbon atom or a hetero atom.

R1 and R2 of the formula 7 each represent an alkyl group or an alkyl group containing a hetero atom, preferably an alkyl group. Moreover, a ring structure which is formed by bonding R1 with R2 via a carbon atom or a hetero atom, can be introduced. R6 is a C1-C15 tri- or higher valent group or a C1-C15 tri- or higher valent group containing a hetero atom, and examples thereof include a trivalent or higher alkylene group, a trivalent or higher alkylene group containing a hetero atom, and structures derived from various trihydric or higher alcohol compounds. Among them, preferred are the structure represented by the formula 8, which is derived from glycerin, and the structure represented by the formula 9, which is derived from trimethylol propane.

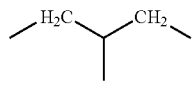

Formula 8

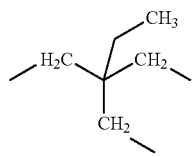

Formula 9

As for the (meth)acrylic acid ester containing the trivalent group represented by the formula 8, preferred is a compound having the structure represented by the following formula 10.
As for the (meth)acrylic acid ester containing the trivalent group represented by the formula 9, preferred is a compound having the structure represented by the following formula 11.

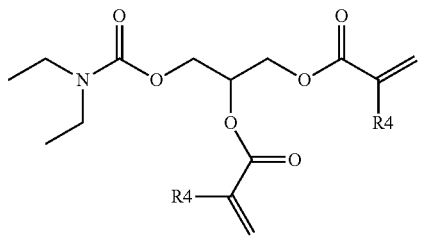

Formula 10

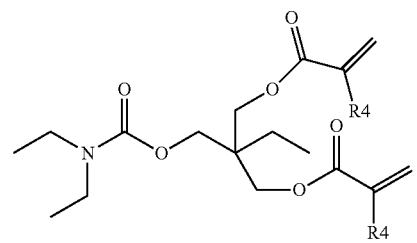

Formula 11

In the formulae 10 and 11, R4 represents a hydrogen atom or a methyl group.

The (meth)acrylic acid ester of the present invention has in its molecular structure a urethane structure that does not include a protic NH structure. Due to the intermolecular interaction caused by an appropriate polarity of the aforementioned structure, the (meth)acrylic acid ester comes close as a reactive monomer to reduce a distance between polymerizing sites during polymerization. Further, as there are two or more polymerizable (meth)acrylic acid ester structures in a molecule, reactivity and curing ability are improved. These urethane structures do not contain a hydrogen atom, and due to such characteristics, generated intermolecular interaction contributes to maintain high variance of molecular motions compared to that with the intermolecular interaction between monomer compounds containing conventional urethane structure via a hydrogen bond. Further more, as the (meth)acrylic acid ester of the present invention is a compound having a relatively small molecular weight, increase in viscosity of the monomer tends to be inhibited, and therefore the (meth)acrylic acid ester of the present invention is suitable for use in an ink.

A molecular weight of the (meth)acrylic acid ester is appropriately selected depending on the intended purpose without any limitation, but it is preferably 100 to 500, more preferably 150 to 400, and even more preferably 150 to 350. When the molecular weight thereof is smaller than 100, the volatility is high, and therefore odor may be strong. When the molecular weight thereof is greater than 500, the fluidity thereof is poor, and it may be difficult to handle. On the other hand, when the molecular weight thereof is 100 to 500, it is advantageous because volatility and odor are suppressed and it is easy to handle.

Specific preferable examples of the (meth)acrylic acid ester of the present invention are listed below. Note that, in the following formulae, "n" represents an integer of 2 to 4.

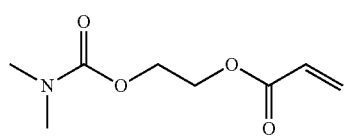

A-1

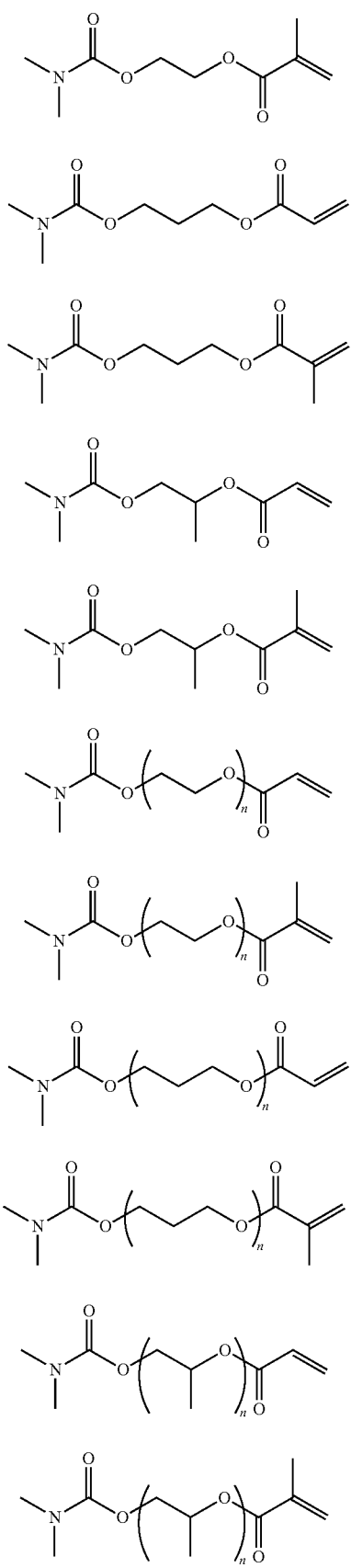
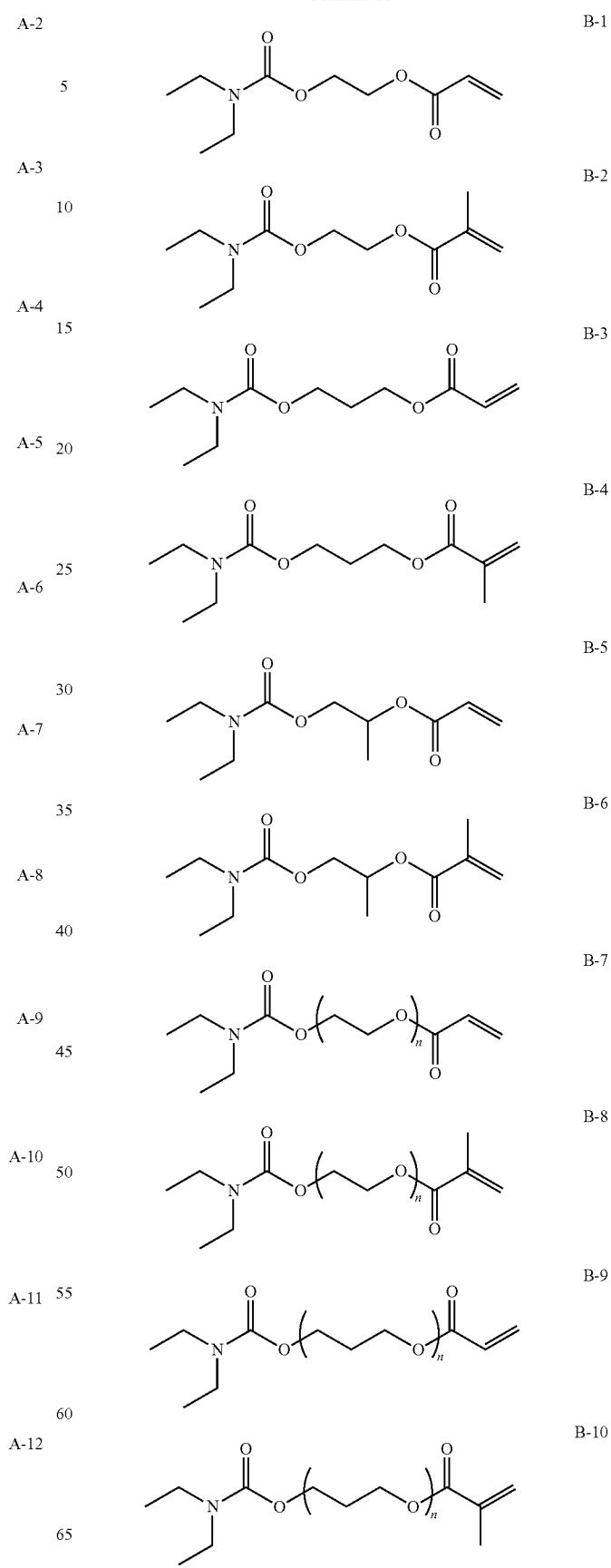

B-11
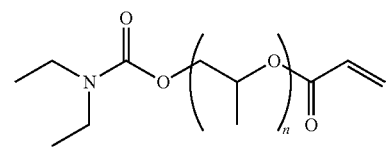
B-12
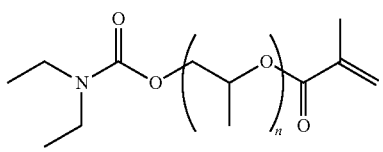
C-1
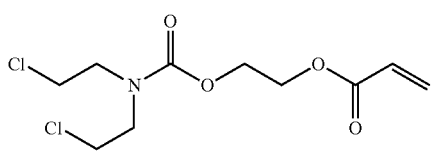
C-2
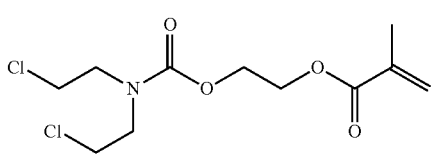
C-3
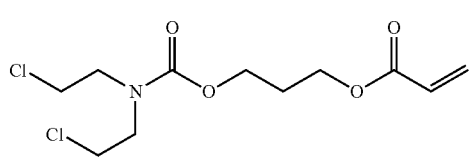
C-4
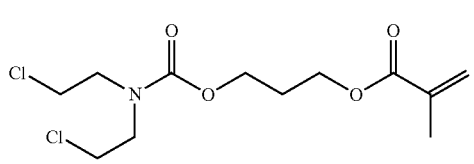
C-5
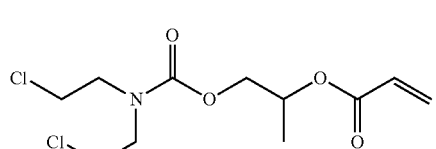
C-6
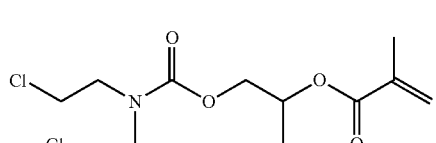
C-7
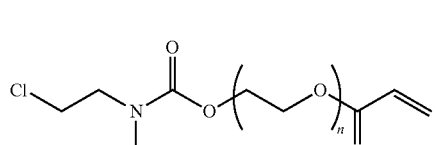
C-8
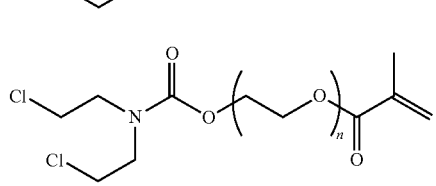
C-9
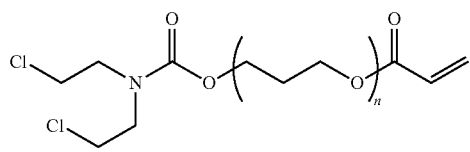
C-10
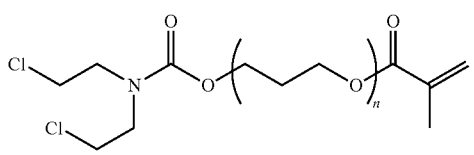
C-11
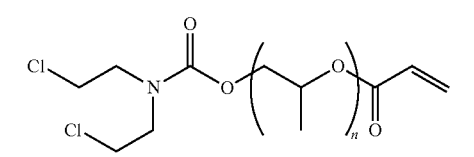
C-12
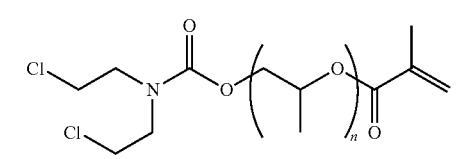
D-1
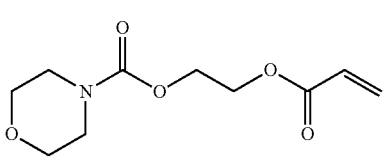
D-2
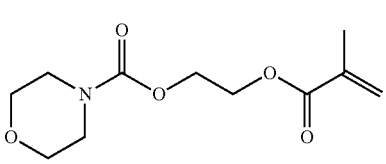
D-3
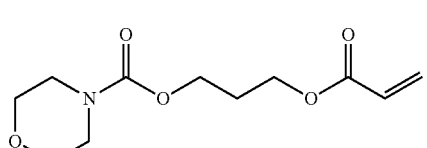
D-4
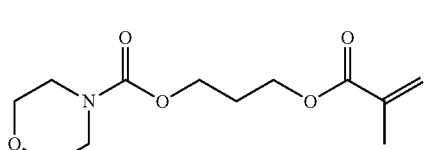
D-5
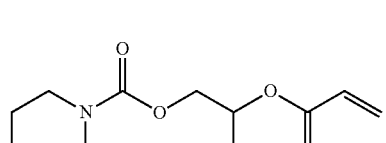
D-6
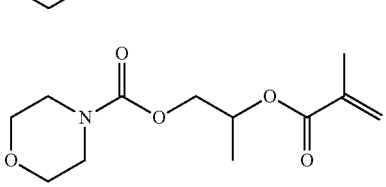

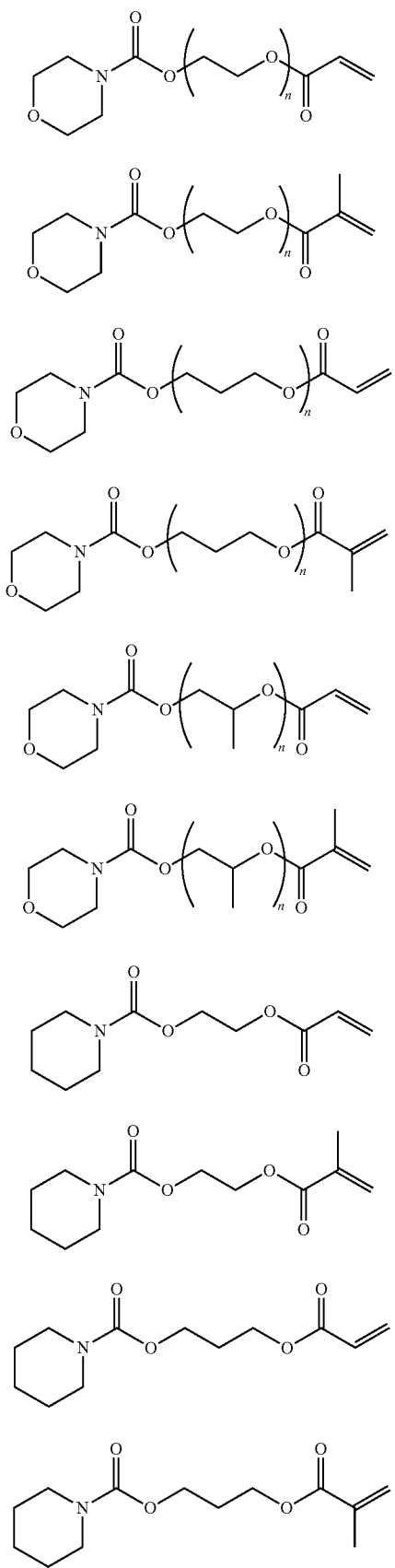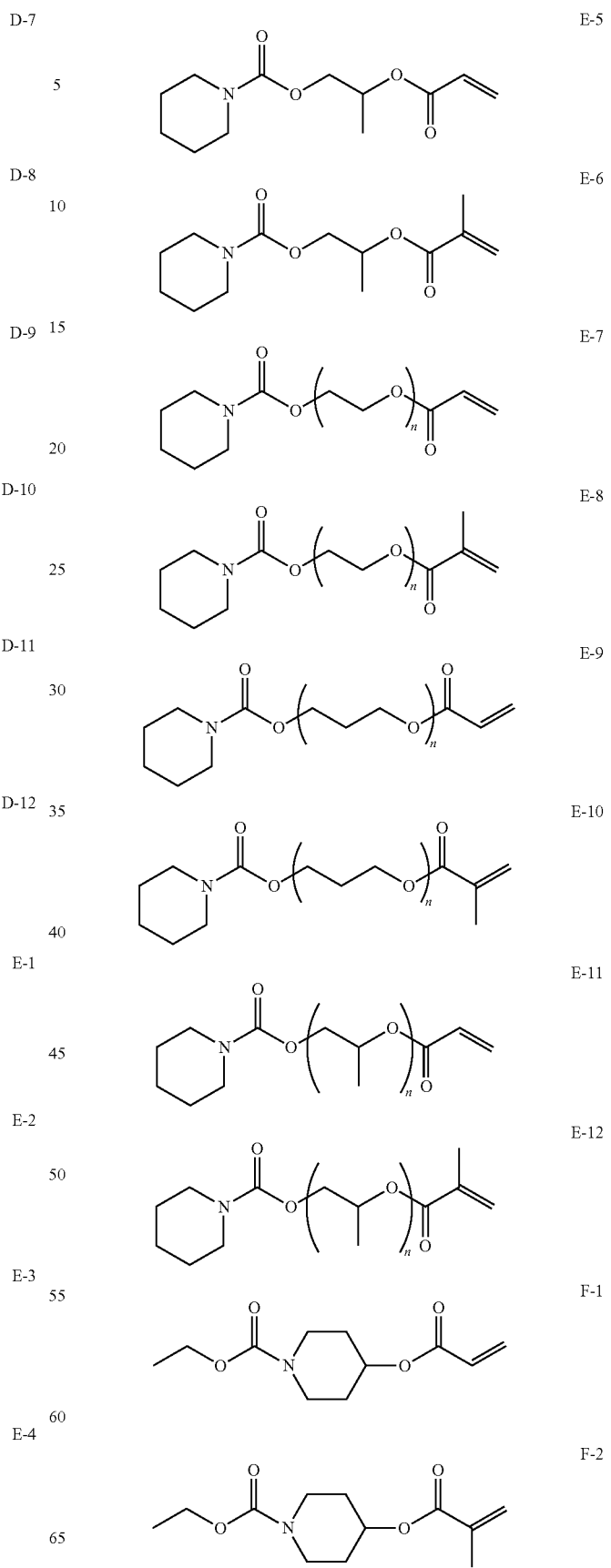

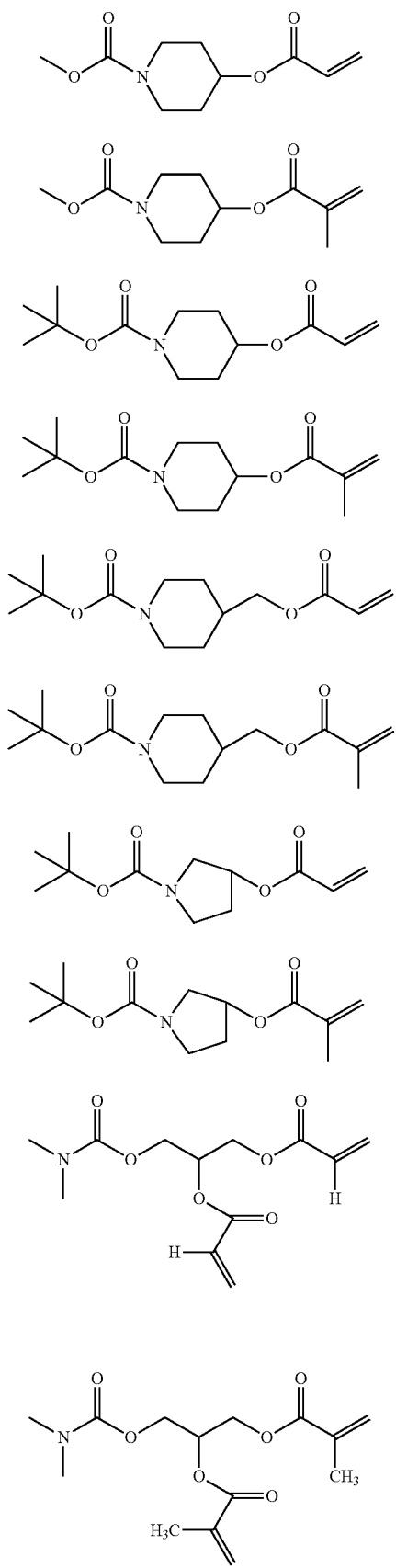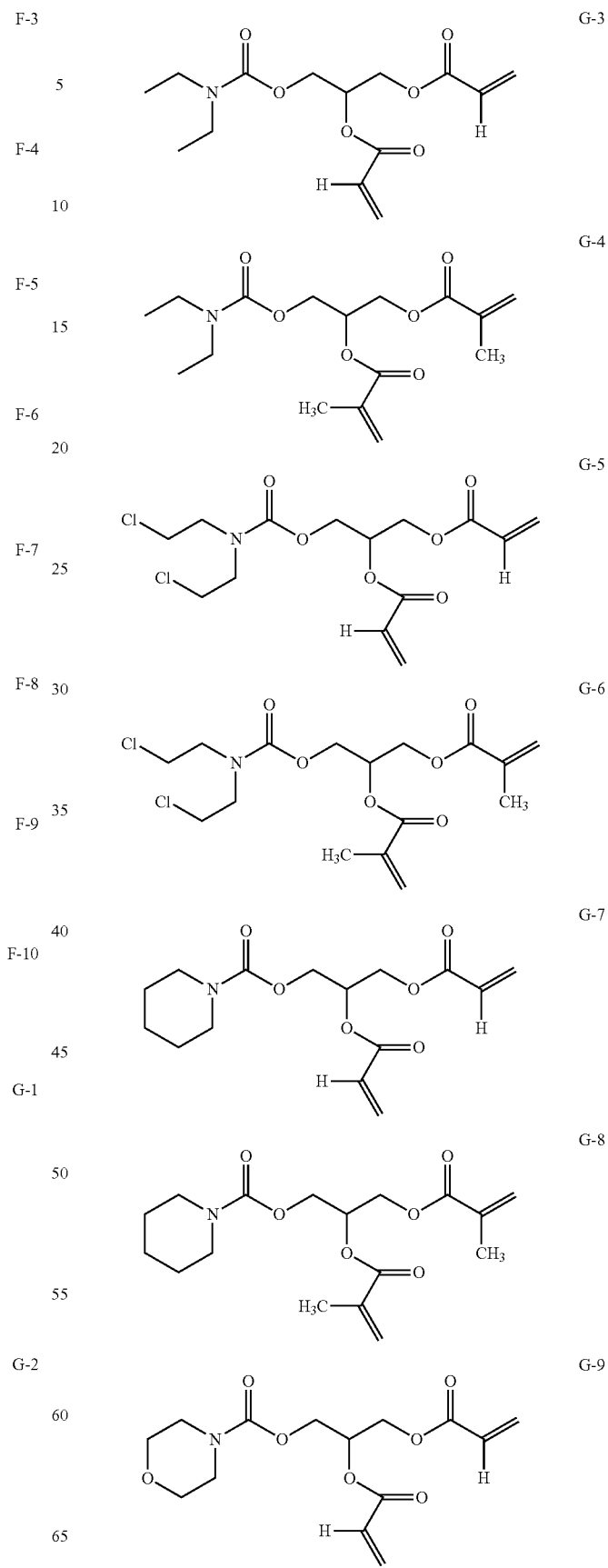

G-10
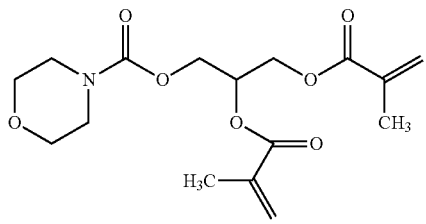
H-1
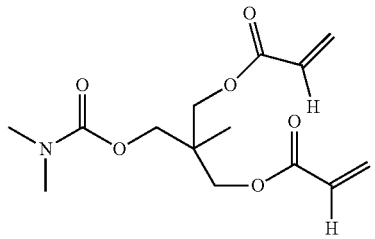
H-2
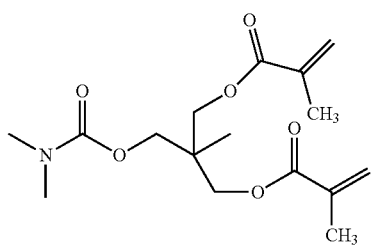
H-3
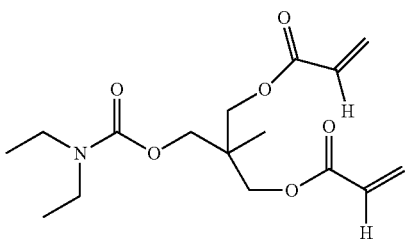
H-4
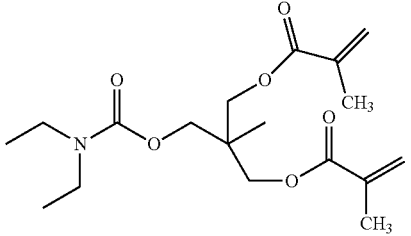
H-5
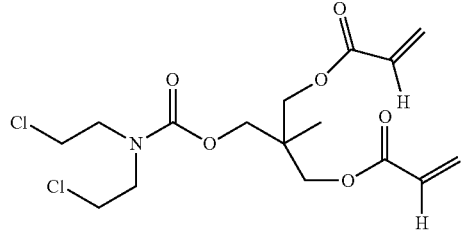
H-6
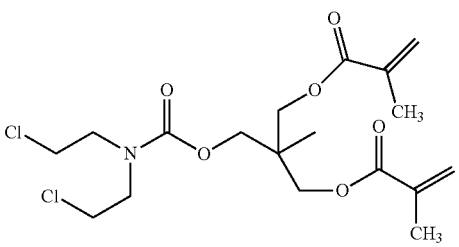
H-7
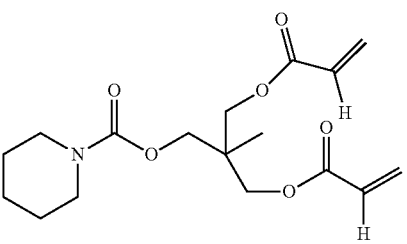
H-8
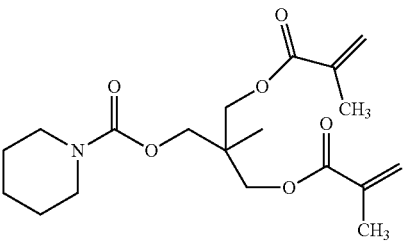
H-9
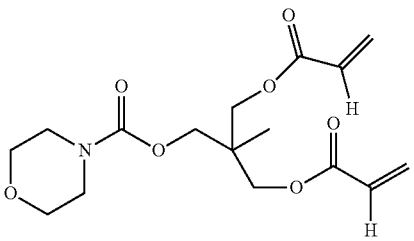
H-10
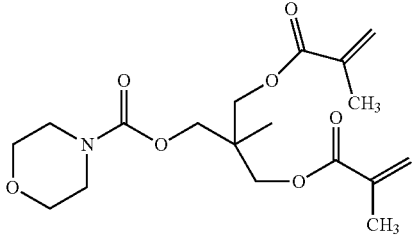
J-1
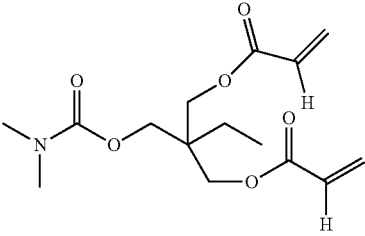

J-2 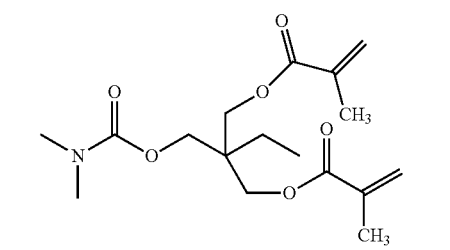
J-3 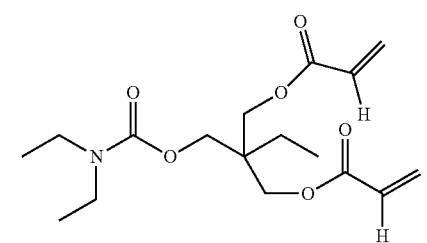
J-4 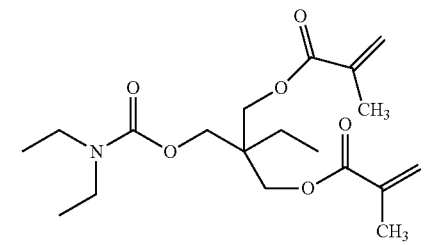
J-5 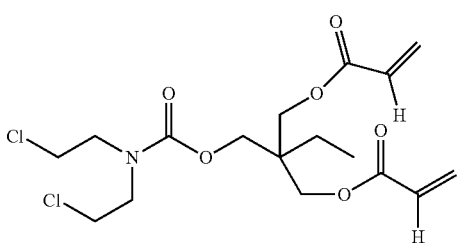
J-6 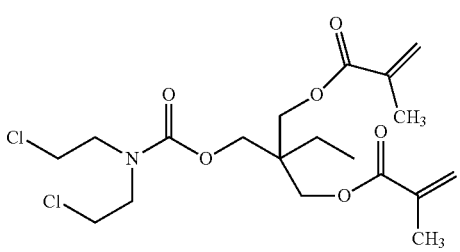
J-7 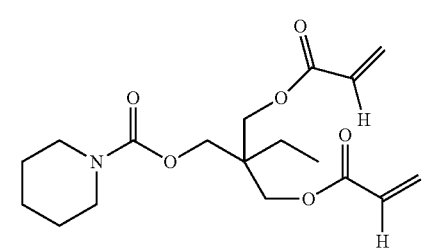
J-8 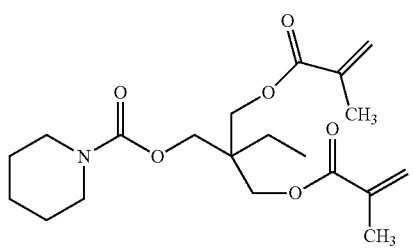
J-9 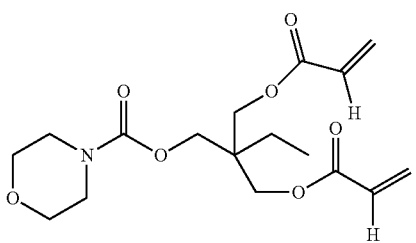
J-10 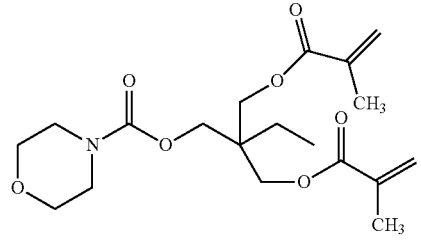
K-1 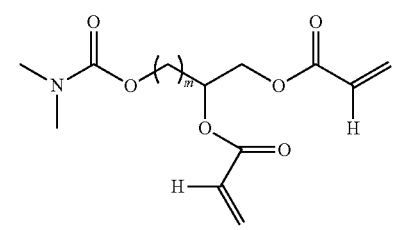
K-2 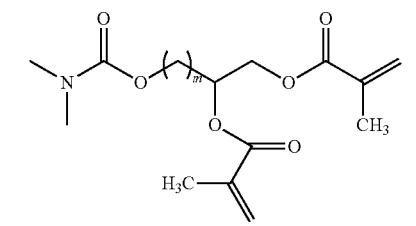
K-3 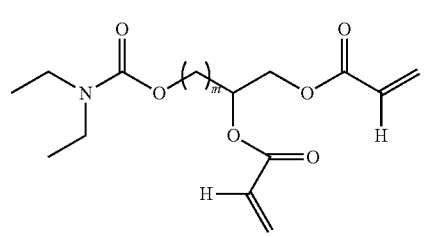

K-4
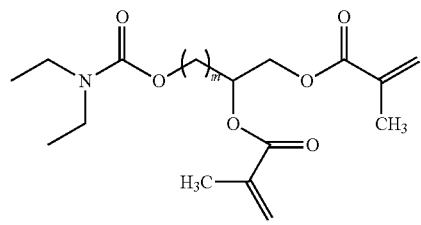
K-5
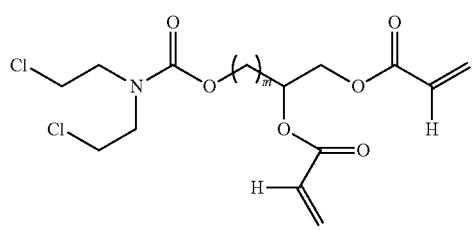
K-6
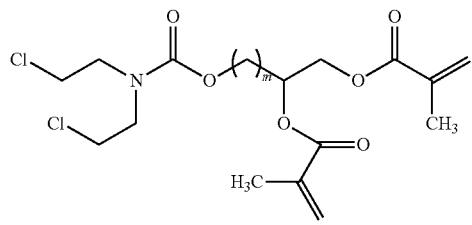
K-7
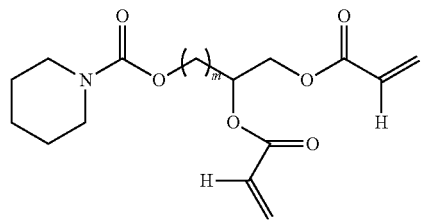
K-8
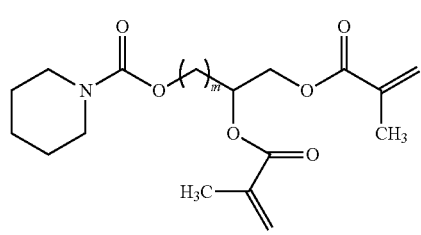
K-9
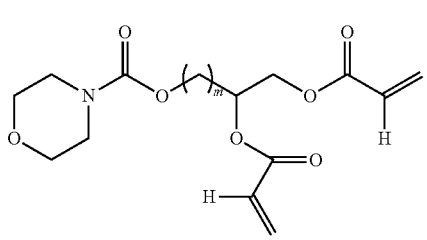
K-10
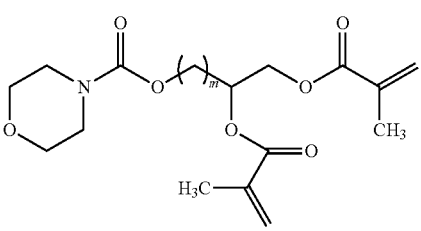
In the formulae above, m is an integer of 2 or greater, preferably 2, 3, 4, 5, or 8.
L-1
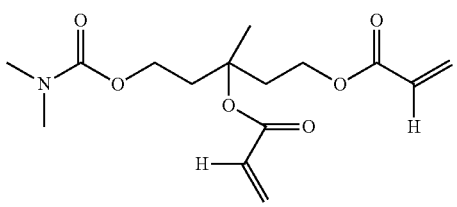
L-2
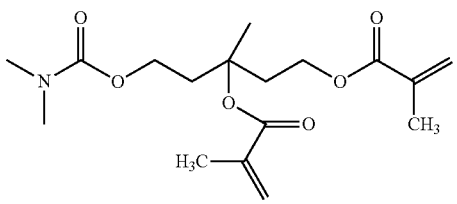
L-3
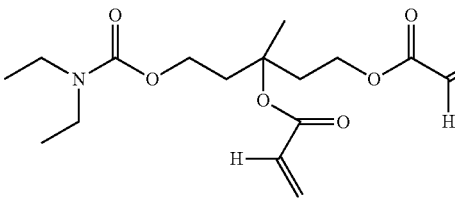
L-4
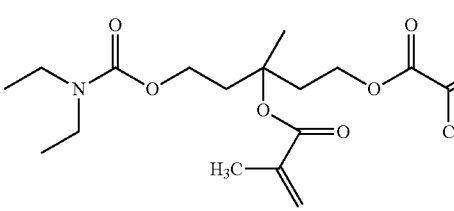
L-5
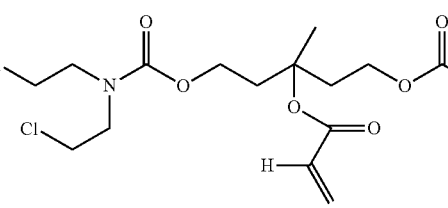
L-6
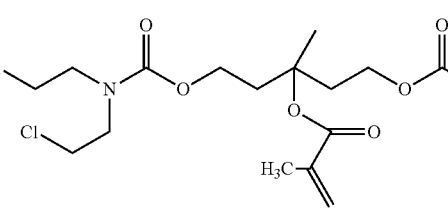
L-7
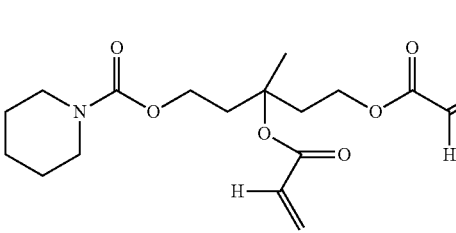

-continued
L-8
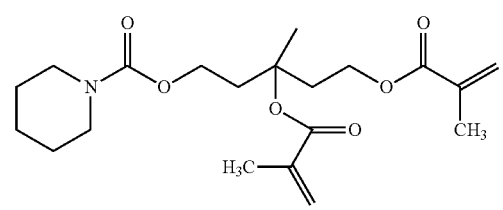
L-9
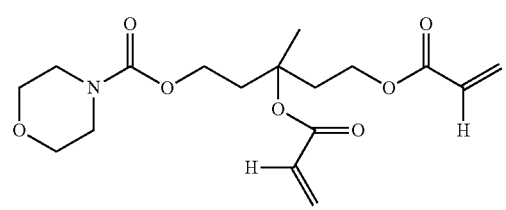
L-10
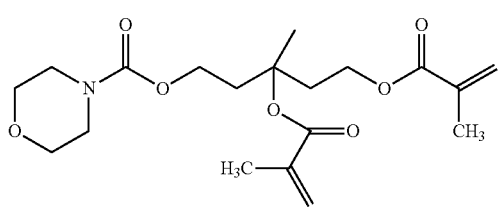
M-1
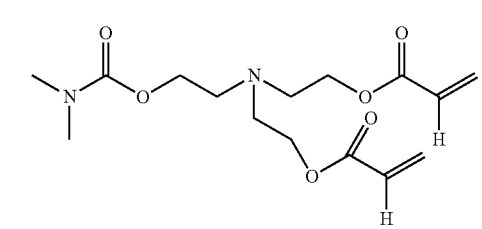
M-2
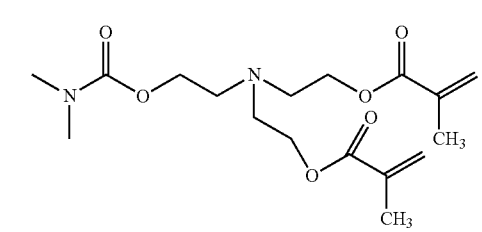
M-3
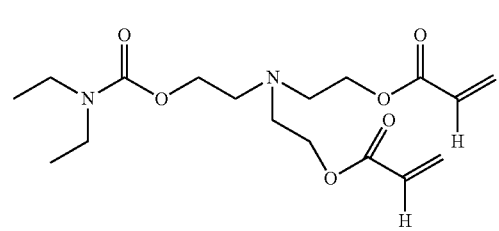
M-4
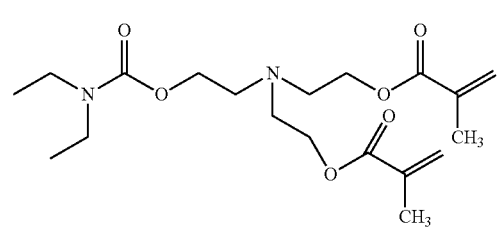
-continued
M-5
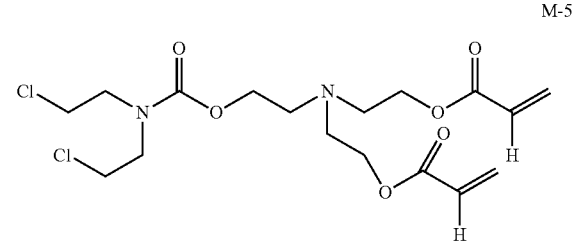
M-6
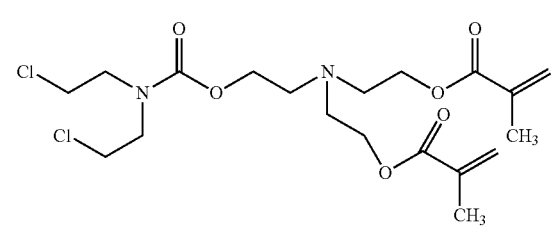
M-7
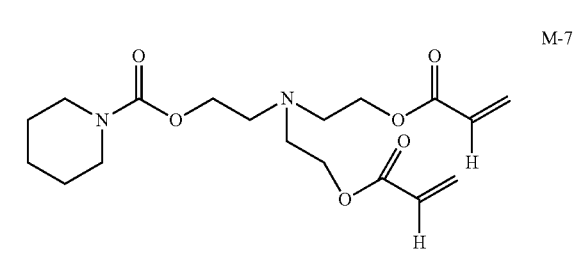
M-8
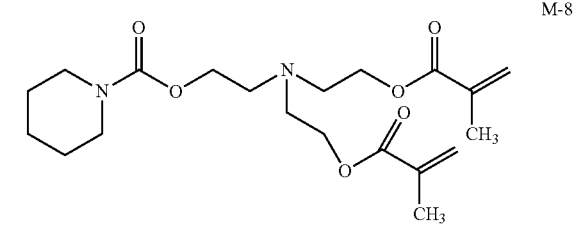
M-9
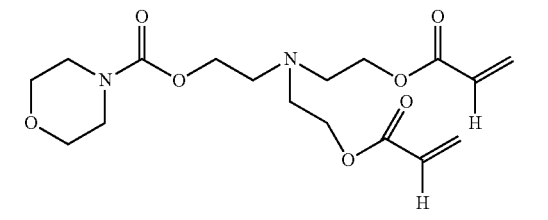
M-10
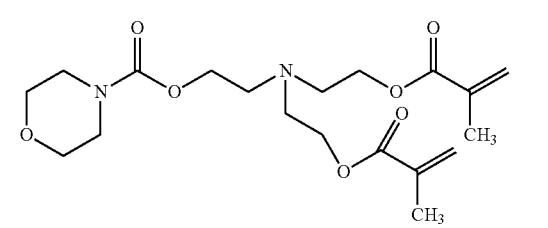

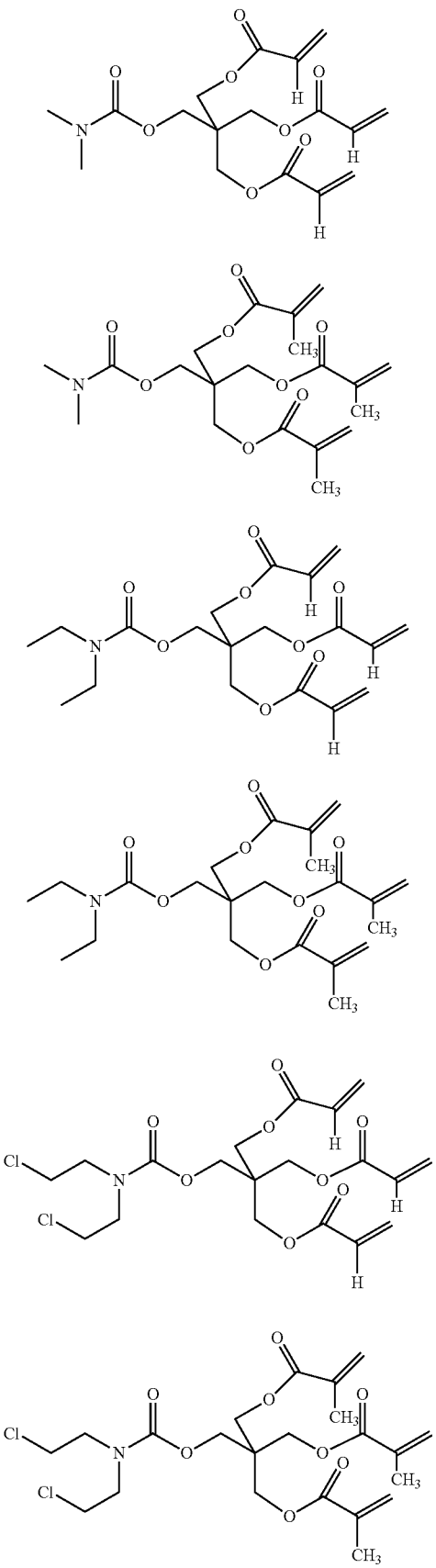
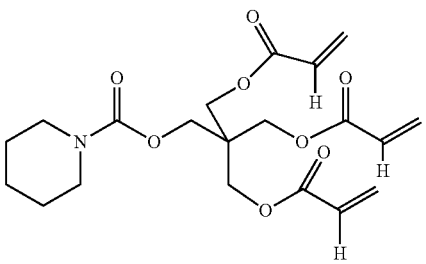
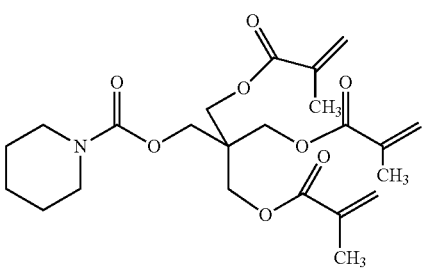
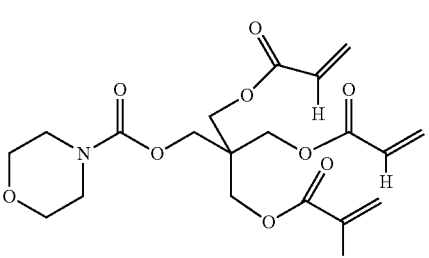
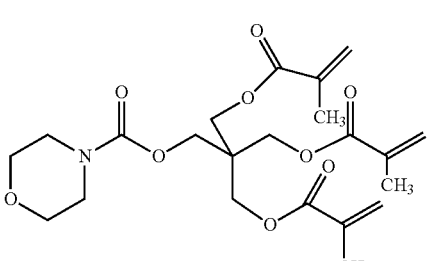

(Activation Energy Ray Curing Composition)

The activation energy ray curing composition of the present invention contains at least the (meth)acrylic acid ester of the present invention, and may further contain optional substances, such as another polymerizable compound, a polymerization initiator, a sensitizing agent, and a cosensitizing agent, if necessary.

(Inkjet Recording Ink)

The inkjet recording ink of the present invention contains at least the activation energy ray curing composition of the present invention, preferably further contains a colorant, and may further contain optional substances, such as another polymerizable compound, a sensitizing agent, and a cosensitizing agent, if necessary.

The (meth)acrylic acid ester of the present invention is blended with a polymerization initiator to form an activation energy ray curing composition, which can be suitably used as an inkjet recording ink.

<Polymerization Initiator>

The polymerization initiator includes, for example, a radical polymerization initiator, a cationic polymerization initiator, and an anionic polymerization initiator. Among them, the radical polymerization initiator and the anionic polymerization initiator are preferable, and the radical polymerization initiator is particularly preferable.

The polymerization initiator can be appropriately selected depending on a type of the (meth)acrylic acid ester for use, or an intended use (e.g., use as an ink).

In a case of an ink, the polymerization initiator is a compound that absorbs external energy to generate a polymerization initiating seed. The external energy used to initiate polymerization is roughly classified into heat and activation energy rays, for which a thermal polymerization initiator and photopolymerization initiator are used respectively. Examples of the activation energy rays include γ-rays, β-rays, electron beams, UV rays, ultraviolet rays, and IR rays. Moreover, as for the thermal polymerization initiator and photo polymerization initiator, compounds known in the art can be used.

Examples of the radical polymerization initiator include (a) aromatic ketone, (b) an acylphosphine oxide compound, (c) an aromatic onium salt compound, (d) organic peroxide, (e) a thio compound, (f) a hexaaryl biimidazole compound, (g) a ketoxime compound, (h) a borate compound, (i) an azinium compound, (j) a metallocene compound, (k) an active ester compound, (l) a compound having a carbon-halogen bond, and (m) an alkyl amine compound. These radical polymerization initiators may be used independently or in combination.

Specific examples of the radical polymerization initiator include benzophenone, Michler's ketone, 4,4'-bis(diethylamino)benzophenone, xanthone, thioxanthone, isopropylxanthone, 2,4-diethylthioxanthone, 2-ethylanthraquinone, acetophenone, 2-hydroxy-2-methylpropiophenone, 2-hydroxy-2-methyl-4'-isopropylpropiophenone, 1-hydroxycyclohexylphenyl ketone, isopropyl benzoin ether, isobutyl benzoin ether, 2,2-diethoxyacetophenone, 2,2-dimethoxy-2-phenylacetophenone, comphorquinone, benzanthrone, 2-methyl-1-[4-(methylthio)phenyl]-2-morpholinopropan-1-one, 2-benzyl-2-dimethylamino-1-(4-morpholinophenynb-utanone-1,4-dimethylamino ethyl benzoate, 4-dimethylamino isoamyl benzoate, 4,4'-di(t-butylperoxycarbonyl) benzophenone, 3,4,4'-tri(t-butylperoxycarbonyl) benzophenone, 3,3',4,4'-tetra(t-butylperoxycarbonyl) benzophenone, 3,3',4,4'-tetra(t-hexylperoxycarbonyl) benzophenone, 3,3'-di(methoxycarbonyl)-4,4'-di(t-butylperoxycarbonyl)benzophenone, 3,4'-di(methoxycarbonyl)-4,3'-di(t-butylperoxycarbonyl) benzophenone, 4,4'-di(methoxycarbonyl)-3,3'-di(t-butylperoxycarbonyl)benzophenone, 1,2-octanedione,1-[4-(phenylthio)phenyl]-2-(o-benzoyloxime), 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4-[p-N,N-di(ethoxycarbonylmethyl)]-2,6-di(trichloromethyl)-s-triazine, 1,3-bis(trichloromethyl)-5-(2'-chlorophenyn-s-triazine, 1,3-bis(trichloromethyl)-5-(4'-methoxyphenyl)-s-triazine, 2-(p-dimethylaminostyryl)benzoxazole, 2-(p-dimethylaminostyryl)benzothiazole, 2-mercapto benzothiazole, 3,3'-carbonylbis(7-diethylaminocoumarin), 2-(o-chlorophenyl)-4,4',5,5'-tetraphenyl-1,2'-biimidazole, 2,2'-bis(2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinopropionyl)-9-n-dodecylcarbazole, 1-hydroxycyclohexylphenyl ketone, bis(η5-2,4-cyclopentandien-1-yl)-bis[2,6-difluoro-3-(1H-pyrrol-1-yl)phenyl]titanium, bis(2,4,6-trimethylbenzoyl)phenyl phosphine oxide, and 2,4,6-trimethylbenzoyldiphenyl phosphine oxide.

Among them, preferred are bis(2,4,6-trimethylbenzoyl) phenyl phosphine oxide (product name: IRGACURE 819, manufactured by BASF Japan Ltd.) or 2,4,6-trimethylbenzoyldiphenyl phosphine oxide (product name: DAROCUR TPO, manufactured by BASF Japan Ltd.), 1-hydroxycyclohexylphenyl ketone (product name: IRGACURE 184, manufactured by BASF Japan Ltd.), 2-methyl-1-[4-(methylthio)phenyl]-2-morpholinopropan-1-one (product name: IRGACURE 907, manufactured by BASF Japan Ltd.), and 2-dimethylamino-2-(4-methylbenzyl)-1-(4-morpholin-4-yl-phenyl)butan-1-one (product name: IRGACURE 379, manufactured by BASF Japan Ltd.), because these have high compatibility to other substances contained in the ink composition, and a resulting ink can be cured with a small dose of UV radiation.

An amount of the polymerization initiator is preferably in the range of 1% by mass to 50% by mass, more preferably in the range of 2% by mass to 40% by mass, and even more preferably in the range of 5% by mass to 30% by mass, relative to a total mass of the (meth)acrylic acid ester, and another polymerizable compound and a colorant, which are described later as optional substances. In the case where the polymerization initiator is used in combination with the below-described sensitizing agent, a mass ratio of the polymerization initiator to the sensitizing agent (the polymerization initiator/the sensitizing agent) is preferably 200/1 to 1/200, more preferably 50/1 to 1/50.

An amount of the (meth)acrylic acid ester in the ink is preferably 20% by mass to 98% by mass, more preferably 30% by mass to 90% by mass, and even more preferably 30% by mass to 80% by mass. The (meth)acrylic acid ester may be used independently, or two or more thereof may be used in combination.

To the ink of the present invention, in addition to the aforementioned substances, other substances can be blended for improving properties thereof, provided that they do not adversely affect an obtainable effect of the present invention. These optional substances will be explained hereinafter.

<Colorant>

The ink of the present invention may contain a colorant, and use of such ink can realize formation of a color image. The colorant is appropriately selected conventional colorants, such as a pigment, an oil-soluble dye, a water-soluble dye, and a disperse dye, without any limitation.

As for the colorant, the pigment or oil-soluble dye that excels in weather resistance and color reproducibility is preferable, and the pigment is more preferable. Moreover, as for the colorant suitable used in an ink composition of the present invention, preferably selected is a compound that does not function as a polymerization inhibitor to a polymerization reaction that is a curing reaction, so as not to reduce sensitivity of a curing reaction induced by activation energy rays.

The pigment is not particularly limited, and examples thereof include organic or inorganic pigments of the following numbers specified with a color index. These are appropriately selected for use depending on the intended purpose.

Examples of a red or magenta pigment include: Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, 257; Pigment Violet 3, 19, 23, 29, 30, 37, 50, and 88; and Pigment Orange 13, 16, 20, and 36.

Examples of a blue or cyan pigment include Pigment Blue 1, 15, 15:1, 15:2, 15:3, 15:4, 15:6, 16, 17-1, 22, 27, 28, 29, 36, and 60.

Examples of a green pigment include Pigment Green 7, 26, 36, and 50.

Examples of a yellow pigment include Pigment Yellow 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, and 193.

Examples of a black pigment include Pigment Black 7, 28, and 26. Examples of a white pigment include Pigment White 6, 18, and 21.

The oil-soluble dye for use in the ink of the present invention will be explained. The term "oil-soluble dye" used in the present specification means a dye substantially insoluble to water. Specifically, the solubility thereof to water at 25° C. (i.e., the weight of the dye dissolved to 100 g of water) is 1 g or less, preferably 0.5 g or less, and more preferably 0.1 g or less. Accordingly, the oil-soluble dye includes a pigment that is insoluble to water, or an oil-soluble dye. Among them, preferred is an oil-soluble dye.

Examples of a yellow dye of the oil-soluble dye include: aryl or heteryl azo dyes containing, as a coupling substance, phenols, naphthols, anilines, pyrazons, pyridones, or chain-opening active methylene compounds; azo methine dyes containing chain-opening active methylene compounds as a coupling substance; methine dyes such as benzylidene dyes and monomethine oxonol dyes; and quinone dyes such as naphthoquinone dyes, and anthraquinone dyes. Other examples of dyes include quinophthalone dyes, nitro-nitroso dyes, acridine dyes, and acridinone dyes.

Examples of a magenta dye of the oil-soluble dye include: aryl or heteryl azo dyes containing, as a coupling substance, phenols, naphthols, anilines; azo methine dyes containing, as a coupling substance, pyrazolones and pyrazolotriazoles; methine dyes such as arylidene dyes, styryl dyes, merocyanine dyes, oxonol dyes; carbonium dyes such as diphenyl methane dyes, triphenyl methane dyes, xanthene dyes; quinone dyes such as naphthoquinone, anthraquinone, and anthrapyridone; and condensed polycyclic dyes such as dioxazine dyes.

Examples of a cyan dye of the oil-soluble dye include: indoaniline dyes, indophenol dyes, or azomethine dyes containing pyrrolotriazoles as a coupling substance; polymethine dyes such as cyanine dyes, oxonol dyes, merocyanine dyes; carbonium dyes such as diphenyl methane dyes, triphenyl methane dyes, and xanthene dyes; phthalocyanine dyes; anthraquinone dyes; aryl or heteryl azo dyes containing, as a coupling substance, phenols, naphthols, or anilines; and indigo, thio indigo dyes.

Specific preferable examples of the oil-soluble dye include: C.I. Solvent Black 3, 7, 27, 29 and 34; C.I. Solvent Yellow 14, 16, 19, 29, 30, 56, 82, 93 and 162; C.I. Solvent Red 1, 3, 8, 18, 24, 27, 43, 49, 51, 72, 73, 109, 122, 132 and 218; C.I. Solvent Violet 3; C.I. Solvent Blue 2, 11, 25, 35, 38, 67 and 70; C.I. Solvent Green 3 and 7; and C.I. Solvent Orange 2.

Moreover, the ink of the present invention may use a disperse dye, provided that it is dissolved in a water-immiscible organic solvent.

Specific preferable examples of the disperse dye include: C.I. Disperse Yellow 5, 42, 54, 64, 79, 82, 83, 93, 99, 100, 119, 122, 124, 126, 160, 184:1, 186, 198, 199, 201, 204, 224, and 237; C.I. Disperse Orange 13, 29, 31:1, 33, 49, 54, 55, 66, 73, 118, 119, and 163; C.I. Disperse Red 54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356, and 362; C.I. Disperse Violet 33; C.I. Disperse Blue 56, 60, 73, 87, 113, 128, 143, 148, 154, 158, 165, 165:1, 165:2, 176, 183, 185, 197, 198, 201, 214, 224, 225, 257, 266, 267, 287, 354, 358, 365, and 368; and C.I. Disperse Green 6:1, and 9.

The colorant is preferably dispersed in an appropriate degree in an ink. For the dispersion, various dispersing devices (e.g., a ball mill, sand mill, ring mill, Attritor, roll mill, agitator, HENSCHEL MIXER, colloid mill, ultrasonic homogenizer, pearl mill, wet jet mill, paint shaker) can be used.

Moreover, it is possible to add a dispersing agent when the colorant is dispersed. A type of the dispersing agent is not particularly limited, but the dispersing agent is preferably a polymer dispersing agent. The dispersing agent is preferably added in an amount of 1 part by mass to 50 parts by mass relative to 100 parts by mass of the colorant.

The colorant may be used independently, or in combination, depending on the intended use of an ink.

In the case where a colorant that is present as a solid in the ink, such as a pigment, is used, the average particle diameter of the colorant particles is preferably 0.005 μm to 0.5 μm, more preferably 0.01 μm to 0.45 μm, and even more preferably 0.015 μm to 0.4 μm. It is preferred that the selection of the colorant, dispersing agent, and dispersion medium, dispersion conditions, and filtration conditions be selected to give the aforementioned range of the average particle diameter. By controlling the particle diameters in this manner, clogging of a head nozzle can be inhibited, and therefore storage stability, transparency, and curing sensitivity of the ink can be maintained.

An amount of the colorant is appropriately selected depending on the intended use of the ink, but it is typically preferably 0.5% by mass to 10% by mass, more preferably 1% by mass to 8% by mass relative to a total amount of the ink, in view of physical properties or coloring ability of the ink. In the case of a white ink composition using a white pigment (e.g. titanium oxide) as the colorant, an amount of the colorant is preferably 5% by mass to 30% by mass, more preferably 10% by mass to 25% by mass relative to a total amount of the ink, in order to maintain masking characteristics.

<Another Polymerizable Compound (Monomer)>

The ink of the present invention can contain a polymerizable compound other than the (meth)acrylic acid ester (may referred to as "another polymerizable compound" hereinafter). Examples of another polymerizable compound that can be used in combination include a radical polymerizable compound, a cationic polymerizable compound, and an anionic polymerizable compound.

The radical polymerizable compound is not particularly limited, provided that it has at least one radical polymerizable ethylene unsaturated bond in a molecule thereof, and the radical polymerizable compound includes those having a chemical form of a monomer, oligomers, and polymer. One type of the radical polymerizable compound may be used in combination, or two or more types thereof may be used with an appropriate ratio in order to improve the intended properties.

Examples of the radical polymerizable compound include unsaturated carboxylic acid (e.g., acrylic acid, methacrylic acid, itaconic acid, crotonic acid, isocrotonic acid, and maleic acid), a salt thereof, a derived compound thereof, anhydrate containing an ethylene unsaturated group, acrylonitrile, styrene, and various radical polymerizable compounds (e.g., unsaturated polyester, unsaturated polyether, unsaturated polyamide, and unsaturated urethane).

Specific examples thereof include: acrylic acid derivatives, such as 2-hydroxyethyl acrylate, butoxy ethyl acrylate, carbitol acrylate, cyclohexyl acrylate, tetrahydrofurfuryl acrylate, benzyl acrylate, bis(4-acryloxy polyethoxyphenyl)propane, neopentyl glycol diacrylate, ethoxylated neopentyl glycol diacrylate, propoxylated neopentyl glycol diacrylate, 1,6-hexanediol diacrylate, ethylene glycol diacrylate, diethylene glycol diacrylate, triethylene glycol diacrylate, tetraethylene glycol diacrylate, polyethylene glycol diacrylate, propylene glycol diacrylate, dipropylene glycol diacrylate, tripropylene glycol diacrylate, tetrapropylene glycol diacrylate, polypropylene glycol diacrylate, pentaerythritol triacrylate, pentaerythritol tetraacrylate, dipentaerythritol tetraacrylate, trimethylolpropane triacrylate, tetramethylol methane tetraacrylate, oligoester acrylate, epoxy acrylate; methacrylic acid derivatives such as methyl methacrylate, n-butyl methacrylate, allyl methacrylate, glycidyl methacrylate, benzyl methacrylate, dimethylaminomethyl methacrylate, 1,6-hexanedioldimethacrylate, ethylene glycol dimethacrylate, triethylene glycol dimethacrylate, polyethylene glycol dimethacrylate, polypropylene glycol dimethacrylate, trimethylol ethane trimethacrylate, trimethylolpropane trimethacrylate, 2,2-bis(4-methacryloxy polyethoxyphenyl) propane; acrylamide derivatives, such as N-methylol acryl amide, diacetone acryl amide, 2-hydroxyethyl acryl amide, acryloylmorpholine; and allyl compound derivatives such as allyl glycidyl ether, diallyl phthalate, and triallyl trimellitate. Moreover, commercial products, or known reactive monomers, oligomers, and polymers described in the main body and documents, including data for photoreactive materials in Optical Applied Technologies and Materials Dictionary (edited by the editorial committee of Optical Applied Technologies and Materials Dictionary, Kabushikigaisha Sangyo Gijutsu Service center, published in 2006), can be used.

Further, it is also preferred that a vinyl ether compound be used as the radical polymerizable compound. Examples of the preferably usable vinyl ether compound include: di or trivinyl ether compounds, such as ethylene glycol divinyl ether, ethylene glycol monovinyl ether, diethylene glycol divinyl ether, triethylene glycol monovinyl ether, triethylene glycol divinyl ether, propylene glycol divinyl ether, dipropylene glycol divinyl ether, butanediol divinyl ether, hexanediol divinyl ether, cyclohexane dimethanol divinyl ether, hydroxyethyl monovinyl ether, hydroxynonyl monovinyl ether, and trimethylolpropane trivinyl ether; and monovinyl ether compounds such as ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexane dimethanol monovinyl ether, n-propyl vinyl ether, isopropyl vinyl ether, isopropenyl ether-o-propylene carbonate, dodecyl vinyl ether, diethylene glycol monovinyl ether, and octadecyyl vinyl ether. The vinyl ether compounds may be used independently or in combination.

As for another polymerizable compound, (meth)acrylic acid ester such as (meth)acryl monomer or prepolymer, epoxy monomer or prepolymer, and urethane monomer or prepolymer, is also included.

Specific examples thereof include 2-ethylhexyl diglycol acrylate, 2-hydroxy-3-phenoxypropyl acrylate, 2-hydroxybutyl acrylate, hydroxyl pivalic acid neopentyl glycol diacrylate, 2-acryloyloxy ethyl phthalate, methoxy polyethylene glycol acrylate, tetramethylol methane triacrylate, 2-acryloyloxyethyl-2-hydroxyethyl phthalate, dimethylol tricyclodecane diacrylate, epoxylated phenyl acrylate, 2-acryloyloxy ethyl succinate, acrylate of nonylphenol ethylene oxide adduct, modified glycerin triacrylate, bisphenol A diglycidyl ether acrylic acid adduct, modified bisphenol A diacrylate, phenoxy polyethylene glycol acrylate, 2-acryloyloxyethyl hexahydrophthalate, diacrylate of propylene oxide adduct of bisphenol A, diacrylate of ethylene oxide adduct of bisphenol A, dipentaerythritol hexaacrylate, pentaerythritol triacrylate, tolylene diisocyanate urethane polymer, flexible lactone-modified acrylate, butoxy ethyl acrylate, propylene glycol diglycidyl ether acrylate adduct, pentaerythritol triacrylate, hexamethylene diisocyanate urethane polymer, 2-hydroxyethyl acrylate, methoxy dipropylene glycol acrylate, ditrimethylolpropane tetraacrylate, pentaerythritol triacrylate, hexamethylene diisocyanate urethane polymer, stearyl acrylate, isoamyl acrylate, isomyristyl acrylate, isostearyl acrylate, and lactone-modified acrylate.

Note that, for the selection of the polymerization initiator and another polymerizable compound, other than a combination of the radical polymerizable compound and radical polymerization initiator above, the following a cationic polymerizable compound and cationic polymerization initiator may be used to provide a radical-cationic hybrid curing ink, or the following anionic polymerization and anionic polymerization initiator may be used in combination to provide a radical-anionic hybrid curing ink, depending on purposes.

The cationic polymerizable compound is not particularly limited, provided that it is a compound that starts a polymerization reaction thereof with an acid generated by a photo acid generator, to thereby cure. As for the cationic polymerizable compound, various conventional cationic polymerizable monomers known as photo cationic polymerizable monomer can be used. Examples thereof include various epoxy compounds, vinyl ether compounds and oxetane compounds described in Optical Applied Technologies and Materials Dictionary (edited by the editorial committee of Optical Applied Technologies and Materials Dictionary, Kabushikigaisha Sangyo Gijutsu Service center, published in 2006). Moreover, as for the cationic polymerization initiator (photo acid generator) used in combination with the cationic polymerizable compound, various materials known in the art can be used. Examples thereof include: $B(C_6F_5)_4^-$, $PF_6^-$, $AsF_6^-$, $SbF_6^-$, or $CF_3SO_3^-$ salt (e.g., diazonium, ammonium, iodonium, sulfonium, and phosphonium) of an aromatic onium compound; a sulfonated compound that generates sulfonic acid; halide that generates hydrogen halide upon application of light; and iron-allene complex. These cationic polymerization initiators may be used independently, or in combination.

Examples of the anionic polymerizable compound include various epoxy compounds, lactone compounds, acrylic compounds, and methacrylic compounds. Among them, preferred are the acrylic compounds and methacrylic compounds described as the examples of the radical polymerizable compound. Moreover, examples of the anionic polymerization initiator include, so-called, photo base generators. Specific examples thereof include orthonitrobenzyl carbamate derivatives, orthoacyloxyl derivatives, and orthocarmoyloxime amidine derivatives.

<Sensitizing Agent>

To the ink of the present invention, a sensitizing agent may be added for accelerating decomposition of the polymerization initiator by active ray radiation.

The sensitizing agent becomes in the electron-excited state as a result of absorption of certain activation energy rays. The sensitizing agent of the electron-excited state is brought into contact with the polymerization initiator to initiate an action, such as electron transfer, energy transfer, and generation of heat, to thereby accelerate chemical changes (decomposition, generation of radical, acid or base) of the polymerization initiator. As for the sensitizing agent, a compound corresponding to a wavelength of activation energy rays that generate initiation seeds to the polymerization initiator can be used. The sensitizing agent is preferably a sensitizing dye, and examples thereof include those having the absorption wavelength in the range of 350 nm to 450 nm, as listed below.

Examples of the sensitizing agent include multinucleated aromatics (e.g., pyrene, perylene, triphenylene), xanthenes (e.g., fluorescein, eosin, erythrosine, rhodamine B, and rose bengal), cyanines (e.g., thiacarbocyanine, and oxacarbocyanine), merocyanines (e.g., merocyanine, and carbomerocyanine), thiazines (e.g., thionine, methylene blue, and toluidine blue), acridines (e.g., acridine orange, chloroflavine, and acriflavine), anthraquinones (e.g., anthraquinone), squaryliums (e.g., squarylium), and cumarins (e.g., 7-diethylamino-4-methyl cumarin).

<Cosensitizing Agent>

The ink of the present invention may contain a cosensitizing agent. The cosensitizing agent has a function of further improving sensitivity of the sensitizing dye to activation energy rays, and suppressing inhibition of polymerization by oxygen.

Examples of the cosensitizing agent include: amine compounds such as triethanol amine, p-dimethylamino ethyl benzoate, p-formyldimethylaniline, and p-methylthiodimethylaniline; and thiols and sulfides, such as 2-mercapto benzothiazole, 2-mercaptobenzoxazole, 2-mercapto benzoimidazole, 2-mercapto-4(3H)-quinazoline, and 6-mercapto naphthalene, but the examples thereof are not limited thereto.

<Other Components>

Other components, such as a polymerization inhibitor, and a solvent, may be optionally added to the ink of the present invention.

The polymerization inhibitor is added for enhancing shelf life (storage stability) of the ink. Moreover, the ink of the present invention is optionally heated to make its viscosity low, and then ejected. In this case, the polymerization inhibitor is preferably added to the ink to prevent clogging of a head caused by thermal polymerization.

Examples of the polymerization inhibitor include hydroquinone, benzoquinone, p-methoxy phenol, TEMPO, TEMPOL, and cupferron A1. An amount of the polymerization inhibitor is preferably 200 ppm to 20,000 ppm relative to a total amount of the ink.

The viscosity of the ink of the present invention is preferably 7 mPa·s to 30 mPa·s, more preferably 7 mPa·s to 25 mPa·s in an environment at the time of ejecting, in view of ejecting performance by an inkjet device.

Since the ink of the present invention is an activation energy ray-curing ink, it is preferred that the ink do not contain a solvent. However, a solvent may be added to the ink for the purpose of improving properties, such as adhesion between the cured ink and a recording medium, as long as it does not adversely affect curing speed of the ink. As for the solvent, an organic solvent or water can be used. An amount of the organic solvent is 0.1% by mass to 5% by mass, preferably 0.1% by mass to 3% by mass, relative to a total amount of the ink.

Further, if necessarily, conventional additives including a surfactant, a leveling additive, a matte agent, and resins for adjusting film properties, such as a polyester resin, a polyurethane resin, a vinyl resin, an acryl resin, a rubber resin, and wax can be appropriately selected and added to the ink. Moreover, it is also possible to add a tackifier, which does not cause polymerization inhibition, for improving adhesion of the ink with polyolefin or PET.

EXAMPLES

The present invention is more specifically explained through Examples and Comparative Examples hereinafter, but Examples shall not be construed as to limit the present invention. Note that, in Examples and Comparative below, "%" is "% by mass."

In order to make an effect of the (meth)acrylic acid ester of the present invention clear, inks prepared below have formulations that do not contain various additives including a colorant.

$^1$H-NMR was measured by means of $^1$H-NMR (500 MHz) manufactured by JEOL LTD., and IR was measured by means of FT-IR Spectrum GX manufactured by PERKIN ELMER.

Synthesis Example 1

Synthesis of B-1

To a mixture of ethylene glycol (33.5 g, 540 mmol) and pyridine (20 g), diethylcarbamoyl chloride (12.2 g, 90 mmol) was added gradually at room temperature, followed by allowing the resulting mixture to react at about 45° C. for about 20 hours. The reaction mixture was poured into water (150 mL), and extracted with ethyl acetate. The extract layer was washed with 10% hydrochloric acid and a saturated sodium hydrogen carbonate aqueous solution, followed by drying with sodium sulfate anhydrous. This ethyl acetate solution was concentrated, and the obtained concentrated solution was purified by column chromatography (Wakogel C300, Wako Pure Chemical industries, Ltd., 300 g) to thereby obtain colorless oily matter (10.2 g). It was confirmed from the below-presented measurement results of the $^1$H-NMR and IR that the colorless oily matter was Intermediate Product 1 presented below. The yield was about 70%.

(Intermediate Product 1)

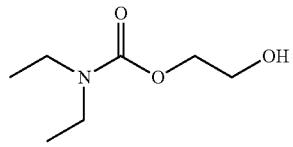

$^1$H-NMR (CDCl$_3$) δ1.13 (t, 6H), 3.30 (br, 4H), 3.80 (m, 2H), 4.24 (m, 2H) IR (NaCl) 3445, 2975, 2937, 2878, 1698, 1681, 1485, 1429, 1381, 1365, 1316, 1278, 1178, 1068, 1024, 972, 939, 892, 770 cm$^{-1}$

Next, Intermediate Product 1 (3.7 g, 23 mmol) was added to dehydrated dichloromethane (70 mL), and the inner atmosphere of the flask was replaced with argon gas, followed by adding triethyl amine (4.1 g, 40 mmol). After cooling the resulting mixture to about −10° C., acryloyl chloride (2.7 g, 30 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (4.5 g). It was confirmed from the below-presented measurement results of the $^1$H-NMR and IR that the pale yellow oily matter was B-1 presented below. The yield was about 91%.

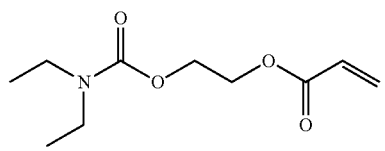

B-1

$^1$H-NMR (CDCl$_3$) δ1.12 (bs, 6H), 3.27 (d, 4H), 4.32 (m, 2H) 4.38 (m, 2H), 5.85-5.87 (dd, 1H), 6.12-6.17 (m, 1H), 6.41-6.45 (dd, 1H)

IR (NaCl) 2976, 2936, 2878, 1728, 1703, 1637, 1620, 1480, 1459, 1428, 1409, 1381, 1366, 1276, 1195, 1170, 1067, 974, 810, 769 cm$^{-1}$

Synthesis Example 2

Synthesis of B-2

Intermediate Product 1 (3.7 g, 23 mmol) obtained in Synthesis Example 1 was added to dehydrated dichloromethane (70 mL), and the inner atmosphere of the flask was replaced with argon gas, followed by adding triethyl amine (4.1 g, 40 mmol). After cooling the resulting mixture to about −10° C., methacryloyl chloride (3.1 g, 30 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain yellow oily matter (4.3 g). It was confirmed from the below-presented measurement results of the $^1$H-NMR and IR that the yellow oily matter was B-2 presented below. The yield was about 82%.

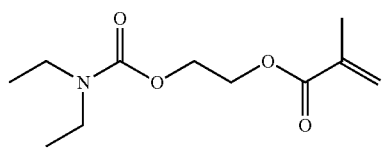

B-2

$^1$H-NMR (CDCl$_3$) δ1.12 (bs, 6H), 1.95 (s, 3H), 3.27 (d, 4H), 4.33 (m, 2H), 4.37 (m, 2H), 5.58 (m, 1H), 6.13 (m, 1H)

IR (NaCl) 2977, 2935, 1704, 1638, 1480, 1453, 1428, 1380, 1320, 1298, 1275, 1226, 1161, 1078, 941, 884, 815, 769, 654 cm$^{-1}$

Synthesis Example 31

Synthesis of D-1

To a mixture of ethylene glycol (18.6 g, 300 mmol) and pyridine (20 g), 4-morpholinylcarbomoyl chloride (7.4 g, 50 mmol) was added gradually at room temperature, followed by allowing the resulting mixture to react at about 45° C. for about 20 hours. The reaction mixture was poured into water (150 mL), and extracted with ethyl acetate. The extract layer was washed with 10% hydrochloric acid and a saturated sodium hydrogen carbonate aqueous solution, followed by drying with sodium sulfate anhydrous. This ethyl acetate solution was concentrated, and the obtained concentrated solution was purified by column chromatography (Wakogel C300, 300 g) to thereby obtain colorless oily matter (6.5 g). It was confirmed from the below-presented measurement results of the $^1$H-NMR and IR that the colorless oily matter was Intermediate Product 2 presented below. The yield was about 75%.

(Intermediate Product 2)

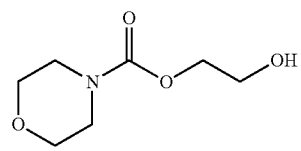

$^1$H-NMR (CDCl$_3$) δ1.54 (bs, 4H), 1.60 (m, 2H), 2.98 (bs, 1H), 3.43 (dd, 4H), 3.81 (m, 2H), 4.24 (m, 2H)

IR (NaCl) 3434, 2938, 2857, 1378, 1475, 1442, 1349, 1266, 1238, 1154, 1073, 1030, 956, 897, 854, 804, 767 cm$^{-1}$

Next, Intermediate Product 2 (3.5 g, 20 mmol) was added to dehydrated dichloromethane (70 mL), and the inner atmosphere of the flask was replaced with argon gas, followed by adding triethyl amine (3.0 g, 30 mmol). After cooling the resulting mixture to about −10° C., acryloyl chloride (2.3 g, 25 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (3.8 g). It was confirmed from the below-presented measurement results of the $^1$H-NMR and IR that the pale yellow oily matter was D-1 presented below. The yield was about 89%.

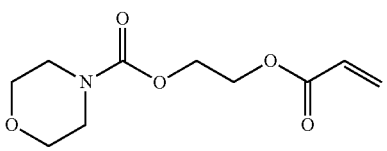

D-1

$^1$H-NMR (CDCl$_3$) δ3.47 (bs, 4H), 3.65 (bs, 4H), 4.34 (m, 2H), 4.38 (m, 2H), 5.85-5.88 (dd, 1H), 6.12-6.18 (m, 1H), 6.41-6.45 (dd, 1H)

IR (NaCl) 2964, 2901, 2860, 1727, 1704, 1636, 1620, 1463, 1434, 1410, 1357, 1296, 1277, 1243, 1190, 1116, 1071, 986, 935, 882, 856, 810, 765, 574 cm$^{-1}$

Synthesis Example 4

Synthesis of D-2

Intermediate Product 2 (3.2 g, 18 mmol) obtained in Synthesis Example 3 was added to dehydrated dichloromethane (70 mL), and the inner atmosphere of the flask was replaced with argon gas, followed by adding triethyl amine (4.0 g, 40 mmol). After cooling the resulting mixture to about −10° C., methacryloyl chloride (2.6 g, 25 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (3.3 g). It was confirmed from the below-presented measurement results of the ¹H-NMR and IR that the pale yellow oily matter was D-2 presented below. The yield was about 75%.

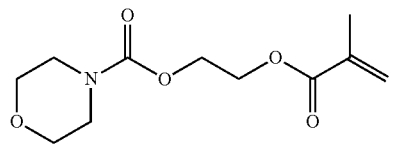

D-2

¹H-NMR (CDCl₃) δ1.95 (s, 3H), 3.47 (bs, 4H), 3.65 (bs, 4H), 4.36 (m, 4H), 5.59 (m, 1H), 6.13 (m, 1H)

IR (NaCl) 2963, 2900, 2856, 1709, 1637, 1433, 1360, 1320, 1298, 1277, 1243, 1168, 1117, 1073, 1048, 1023, 998, 948, 889, 853, 815, 765, 656, 573 cm⁻¹

Synthesis Example 5

Synthesis of E-1

To a mixture of ethylene glycol (18.6 g, 300 mmol) and pyridine (20 g), 1-piperidine carbomoyl chloride (7.4 g, 50 mmol) was added gradually at room temperature, followed by allowing the resulting mixture to react at about 45° C. for about 20 hours. The reaction mixture was poured into water (150 mL), and extracted with ethyl acetate. The extract layer was washed with 10% hydrochloric acid and a saturated sodium hydrogen carbonate aqueous solution, followed by drying with sodium sulfate anhydrous. This ethyl acetate solution was concentrated, and the obtained concentrated solution was purified by column chromatography (Wakogel C300, 300 g) to thereby obtain colorless oily matter (6.5 g). It was confirmed from the below-presented measurement results of the ¹H-NMR and IR that the colorless oily matter was Intermediate Product 3 presented below. The yield was about 75%.

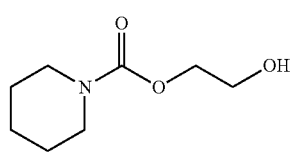

(Intermediate Product 3)

¹H-NMR (CDCl₃) δ1.53 (bs, 4H), 1.59 (m, 2H), 2.98 (bs, 1H), 3.43 (dd, 4H), 3.81 (bs, 2H), 4.24 (m, 2H)

IR (NaCl) 3434, 2938, 2857, 1678, 1475, 1442, 1349, 1266, 1238, 1154, 1073, 1030, 985, 956, 897, 867, 854, 804, 767, 556 cm⁻¹

Next, Intermediate Product 3 (2.8 g, 16 mmol) was added to dehydrated dichloromethane (70 mL), and the inner atmosphere of the flask was replaced with argon gas, followed by adding triethyl amine (3.5 g, 35 mmol). After cooling the resulting mixture to about −10° C., acryloyl chloride (2.3 g, 25 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (3.4 g). It was confirmed from the below-presented measurement results of the ¹H-NMR and IR that the pale yellow oily matter was E-1 presented below. The yield was about 93%.

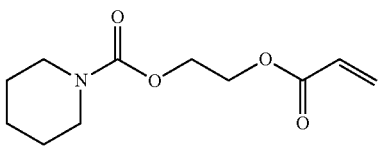

E-1

¹H-NMR (CDCl₃) δ1.52 (bs, 4H), 1.58 (m, 2H), 3.41 (bs, 4H), 4.31 (m, 2H), 4.38 (m, 2H), 5.84-5.87 (dd, 1H), 6.12-6.18 (m, 1H), 6.42-6.46 (dd, 1H)

IR (NaCl) 2939, 2857, 1726, 1703, 1636, 1619, 1472, 1435, 1409, 1375, 1350, 1281, 1262, 1236, 1190, 1151, 1095, 1067, 1024, 985, 929, 880, 853, 809, 765 cm⁻¹

Synthesis Example 6

Synthesis of E-2

Intermediate Product 3 (2.8 g, 16 mmol) obtained in Synthesis Example 5 was added to dehydrated dichloromethane (70 mL), and the inner atmosphere of the flask was replaced with argon gas, followed by adding triethyl amine (3.0 g, 30 mmol). After cooling the resulting mixture to about −10° C., methacryloyl chloride (2.1 g, 20 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain colorless oily matter (3.4 g). It was confirmed from the below-presented measurement results of the ¹H-NMR and IR that the colorless oily matter was E-2 presented below. The yield was about 88%.

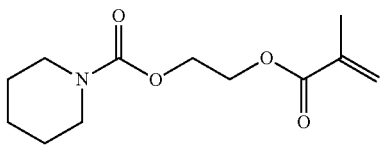

E-2

$^1$H-NMR (CDCl$_3$) δ1.52 (bs, 4H), 1.59 (m, 2H), 1.95 (s, 3H), 3.41 (bs, 4H), 4.32 (m, 2H), 4.36 (m, 2H), 5.59 (m, 1H), 6.13 (bs, 1H)

IR (NaCl) 2939, 2857, 1703, 1638, 1471, 1435, 1376, 1350, 1320, 1298, 1264, 1236, 1168, 1150, 1093, 1023, 954, 911, 885, 853, 814, 765, 654 cm$^{-1}$

Synthesis Example 7

Synthesis of F-1

To dehydrated dichloromethane (70 mL), 4-hydroxy-1-piperidine ethyl carbonate (4.0 g, 23 mmol) was added, and the inner atmosphere of the flask was replaced with argon gas, followed by adding triethyl amine (4.1 g, 40 mmol). After cooling the resulting mixture to about −10° C., acryloyl chloride (2.7 g, 30 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (4.6 g). It was confirmed from the below-presented measurement results of the $^1$H-NMR and IR that the pale yellow oily matter was F-1 presented below. The yield was about 88%.

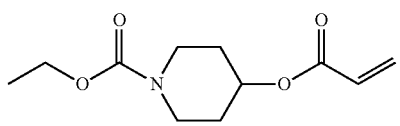

F-1

$^1$H-NMR (CDCl$_3$) δ1.27 (t, 3H), 1.68 (m, 2H), 1.89 (m, 2H), 3.32 (m, 2H), 3.76 (b, 2H), 4.14 (q, 2H), 5.02 (m, 1H), 5.83-5.86 (dd, 1H), 6.10-6.15 (m, 1H), 6.39-6.43 (dd, 1H)

IR (NaCl) 2958, 2869, 1723, 1702, 1635, 1619, 1473, 1434, 1407, 1381, 1356, 1316, 1296, 1274, 1233, 1194, 1138, 1096, 1079, 1028, 985, 941, 892, 811, 768, 670 cm$^{-1}$

Synthesis Example 8

Synthesis of F-2

To dehydrated dichloromethane (70 mL), 4-hydroxy-1-piperidine ethyl carbonate (4.0 g, 23 mmol) was added, and the inner atmosphere of the flask was replaced with argon gas, followed by adding triethyl amine (4.0 g, 40 mmol). After cooling the resulting mixture to about −10° C., methacryloyl chloride (3.1 g, 30 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and washed with sodium sulfate. The resultant was concentrated under reduced pressure, to thereby obtain brown oily matter. The obtained oily matter was purified by column chromatography (Wakogel C300, 250 g), to thereby obtain pale yellow oily matter (3.6 g). It was confirmed from the below-presented measurement results of the $^1$H-NMR and IR that the pale yellow oily matter was F-2 presented below. The yield was about 65%.

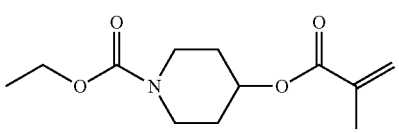

F-2

$^1$H-NMR (CDCl$_3$) δ1.27 (t, 3H), 1.69 (m, 2H), 1.88 (m, 2H), 1.95 (dd, 3H), 3.38 (m, 2H), 3.70 (b, 2H), 4.14 (q, 2H), 5.02 (m, 1H), 5.57 (m, 1H), 6.11 (m, 1H)

IR (NaCl) 2958, 2932, 2869, 1704, 1637, 1472, 1434, 1382, 1354, 1327, 1294, 1274, 1231, 1170, 1137, 1096, 1079, 1029, 941, 910, 870, 837, 815, 768, 653, 611 cm$^{-1}$

Synthesis Example 9

Synthesis of G-3

To a mixture of glycerin (46.0 g, 540 mmol) and pyridine (47 g), diethylcarbamoyl chloride (27.1 g, 200 mmol) was added gradually at room temperature, followed by allowing the resulting mixture to react at about 50° C. for about 15 hours. After removing excess pyridine by concentrating the reaction mixture under reduced pressure, 10% hydrochloric acid was added thereto to make the mixture acidic. The mixture was then concentrated under reduced pressure to remove water, to thereby obtain brown oily matter. The obtained oily matter was extracted with ethyl acetate, and the extract layer was dried with sodium sulfate anhydrous. This ethyl acetate solution was concentrated, and the obtained yellow oily matter (27 g) was purified by column chromatography (Wakogel C300, 400 g) to thereby obtain colorless oily matter (16.1 g). It was confirmed from the below-presented measurement result of the $^1$H-NMR that the colorless oily matter was Intermediate Product 4 presented below. The yield was about 42%.

(Intermediate Product 4)

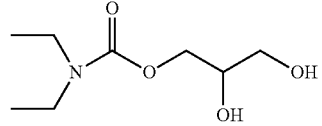

$^1$H-NMR (CDCl$_3$) δ1.13 (t, 6H) 3.23-3.33 (m, 4H), 3.56-3.62 (m, 1H), 3.63-3.69 (m, 1H), 3.73 (d, 1H), 3.77-3.82 (m, 1H), 3.86-3.92 (m, 1H), 4.20 (bs, 2H)

IR (NaCl) 3419, 2974, 2936, 2878, 1681, 1485, 1457, 1431, 1381, 1365, 1316, 1280, 1225, 1180, 1071, 1009, 770 cm$^{-1}$

Next, Intermediate Product 4 (3.4 g, 18 mmol) was added to dehydrated dichloromethane (70 mL), and the inner atmosphere of the flask was replaced with argon gas, followed by adding triethyl amine (5.6 g, 55 mmol). After cooling the resulting mixture to about −10° C., acryloyl chloride (4.1 g, 45 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain colorless oily matter (3.3 g). It was confirmed from the below-presented measurement results of the $^1$H-NMR and IR that the colorless oily matter was G-3 presented below. The yield was about 91%.

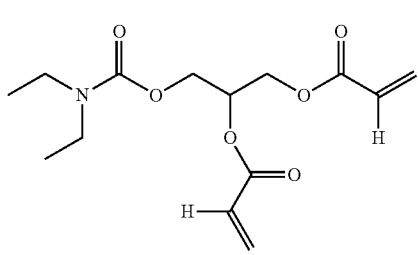

G-3

$^1$H-NMR (CDCl$_3$) δ1.11 (t, 6H), 3.26 (d, 4H), 4.22-4.44 (m, 4H), 5.44 (m, 1H), 5.85-5.90 (dd, 2H), 6.09-6.17 (m, 2H), 6.40-6.46 (dd, 2H)

IR (NaCl) 2976, 1732, 1704, 1636, 1480, 1457, 1429, 1408, 1381, 1273, 1173, 1072, 984, 808, 767 cm$^{-1}$

Synthesis Example 10

Synthesis of G-4

Intermediate Product 4 (6.7 g, 35 mmol) obtained in Synthesis Example 9 was added to dehydrated dichloromethane (70 mL), and the inner atmosphere of the flask was replaced with argon gas, followed by adding triethyl amine (11.1 g, 110 mmol). After cooling the resulting mixture to about −10° C., methacryloyl chloride (9.4 g, 90 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was then concentrated under reduced pressure, to thereby obtain brown oily matter. The obtained oily matter was purified by column chromatography (Wakogel C300, 250 g), to thereby obtain colorless oily matter (7.8 g). It was confirmed from the below-presented measurement results of the $^1$H-NMR and IR that the colorless oily matter was G-4 presented below. The yield was about 68%.

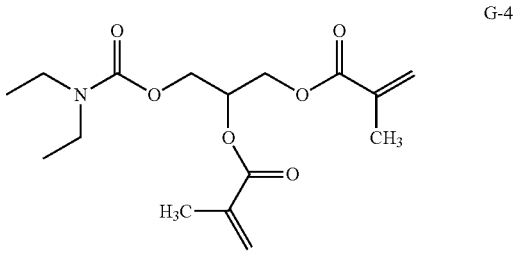 [SMILES: C=C(C)C(=O)OCC(COC(=O)N(CC)CC)OC(=O)C(=C)C]

G-4

$^1$H-NMR (CDCl$_3$) δ1.11 (bs, 6H), 1.94 (s, 6H), 3.25 (d, 4H), 4.25-4.45 (m, 4H), 5.44 (m, 1H), 5.60 (m, 2H), 6.12 (m, 2H)

IR (NaCl) 2977, 2933, 1724, 1706, 1638, 1479, 1456, 1428, 1379, 1319, 1294, 1274, 1226, 1164, 1097, 1074, 1013, 944, 854, 813, 767, 667 cm$^{-1}$

Synthesis Example 11

Synthesis of J-3

To a mixture of trimethylol propane (67.0 g, 600 mmol) and pyridine (47 g), diethylcarbamoyl chloride (27.1 g, 200 mmol) was added gradually at room temperature, followed by allowing the resulting mixture to react at about 50° C. for about 15 hours. After removing excess pyridine by concentrating the reaction mixture under reduced pressure, 10% hydrochloric acid was added thereto to make the mixture acidic. The mixture was then concentrated under reduced pressure to remove water, to thereby obtain brown oily matter. The obtained oily matter was extracted with ethyl acetate, and the extract layer was dried with sodium sulfate anhydrous. This ethyl acetate solution was concentrated, and the obtained green oily matter (32 g) was purified by column chromatography (Wakogel C300, 400 g), to thereby obtain colorless oily matter (17.7 g). It was confirmed from the below-presented measurement result of the $^1$H-NMR that the colorless oily matter was Intermediate Product 5 presented below. The yield was about 38%.

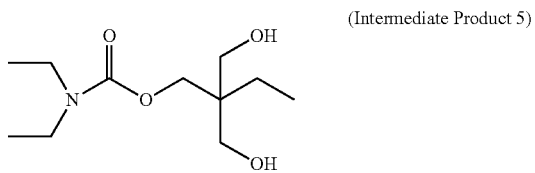 [SMILES: CCN(CC)C(=O)OCC(CC)(CO)CO]

(Intermediate Product 5)

$^1$H-NMR (CDCl$_3$) δ0.89 (t, 3H), 1.14 (t, 6H), 1.28 (q, 2H), 3.23-3.34 (m, 4H), 3.48-3.59 (m, 4H), 3.62-3.66 (m, 2H), 4.23 (s, 2H)

IR (NaCl) 3431, 2970, 2935, 2881, 1678, 1487, 1459, 1431, 1380, 1316, 1279, 1225, 1180, 1069, 1004, 771 cm$^{-1}$

Next, Intermediate Product 5 (3.4 g, 14 mmol) was added to dehydrated dichloromethane (70 mL), and the inner atmosphere of the flask was replaced with argon gas, followed by adding triethyl amine (4.6 g, 45 mmol). After cooling the resulting mixture to about −10° C., acryloyl chloride (3.3 g, 36 mmol) was gradually added dropwise so that the internal temperature of the system was to be in the range of −10° C. to −5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was concentrated under reduced pressure, to thereby obtain brown oily matter. The obtained oily matter was purified by column chromatography (Wakogel C300, 250 g), to thereby obtain pale yellow oily matter (2.1 g). It was confirmed from the below-presented measurement results of the $^1$H-NMR and IR that the pale yellow oily matter was J-3 presented below. The yield was about 43%.

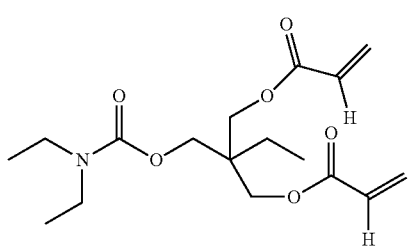

J-3

$^1$H NMR (CDCl$_3$) δ0.94 (t, 3H), 1.12 (t, 6H), 1.55 (q, 2H), 3.26 (d, 4H) 4.09 (s, 2H), 4.16 (s, 4H), 5.84-5.87 (dd, 2H), 6.09-6.15 (m, 2H), 6.38-6.43 (dd, 2H)

IR (NaCl) 2973, 2935, 1730, 1701, 1635, 1558, 1540, 1473, 1457, 1428, 1408, 1380, 1271, 1172, 1064, 987, 809, 786, 768 cm$^{-1}$

Synthesis Example 12

Synthesis of J-4

Intermediate Product 5 (8.1 g, 35 mmol) obtained in Synthesis Example 11 was added to dehydrated dichloromethane (70 mL), and the inner atmosphere of the flask was replaced with argon gas, followed by adding triethyl amine (11.1 g, 110 mmol). After cooling the resulting mixture to about –10° C., methacryloyl chloride (9.4 g, 90 mmol) was gradually added dropwise so that the internal temperature of the system was to be in the range of –10° C. to –5° C. Then, the resulting mixture was stirred for 2 hours at room temperature. The precipitates in the mixture were removed by filtration, and the filtrate was washed with water, a saturated sodium hydrogen carbonate aqueous solution, and a saturated sodium chloride aqueous solution, and dried with sodium sulfate. The resultant was then concentrated under reduced pressure, to thereby obtain brown oily matter. The obtained oily matter was purified by column chromatography (Wakogel C300, 250 g), to thereby obtain colorless oily matter (10.4 g). It was confirmed from the below-presented measurement results of the $^1$H-NMR and IR that the colorless oily matter was J-4 presented below. The yield was about 80%.

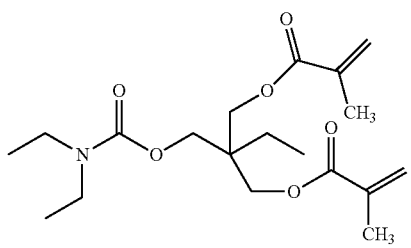

J-4

$^1$H-NMR (CDCl$_3$) δ0.95 (t, 3H), 1.11 (t, 6H), 1.56 (q, 2H), 1.94 (s, 6H), 3.26 (d, 4H), 4.10 (s, 2H), 4.15 (s, 4H), 5.58 (m, 2H), 6.10 (bs, 2H)

IR (NaCl) 2974, 2933, 1722, 1705, 1636, 1558, 1540, 1473, 1457, 1428, 1379, 1321, 1294, 1273, 1226, 1162, 1073, 1014, 942, 813, 785, 768 cm$^{-1}$

Referential Synthesis Example 1

Synthesis of 2-acryloxy ethylethyl sulfide

The following 2-acryloxy ethylethyl sulfide was obtained as colorless oily matter in the same manner as in Synthesis Example 1, provided that diethylcarbamoyl chloride was replaced with 2-(ethylthio)ethanol. The yield was about 83%. The structure of this compound was confirmed by $^1$H-NMR, and IR. $^1$H-NMR (CDCl$_3$) δ1.28 (t, 3H), 2.61 (q, 2H), 2.80 (t, 2H), 4.32 (t, 2H), 5.84-5.87 (dd, 2H), 6.11-6.16 (m, 2H), 6.41-6.45 (dd, 2H)

IR (NaCl) 2967, 2929, 1727, 1636, 1620, 1454, 1407, 1297, 1269, 1183, 1056, 983, 810, 666 cm$^{-1}$

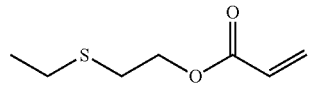

Referential Synthesis Example 2

Synthesis of 2-methacryloxyethylethyl sulfide

The following 2-methacryloxyethylethyl sulfide was obtained as colorless oily matter in the same manner as in Referential Synthesis Example 1, provided that acryloyl chloride was replaced with methacryloyl chloride. The yield was about 82%. The structure of this compound was confirmed by $^1$H-NMR, and IR.

$^1$H-NMR (CDCl$_3$) δ1.28 (t, 3H), 1.95-1.96 (dd, 3H), 2.61 (q, 2H), 2.80 (t, 2H), 4.31 (t, 2H), 5.58-5.59 (m, 1H), 6.12-6.13 (m, 1H)

IR (NaCl) 2965, 2929, 1785, 1719, 1637, 1453, 1404, 1376, 1320, 1296, 1160, 1049, 1011, 975, 942, 814, 653 cm$^{-1}$

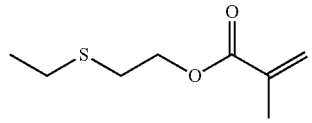

As referential examples, the following commercial products (a) to (e) of monomer compounds were obtained.

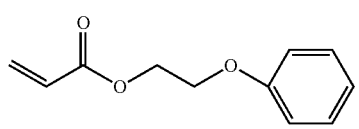

(a)

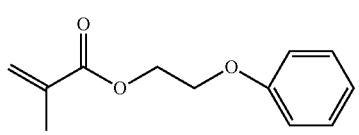

(b)

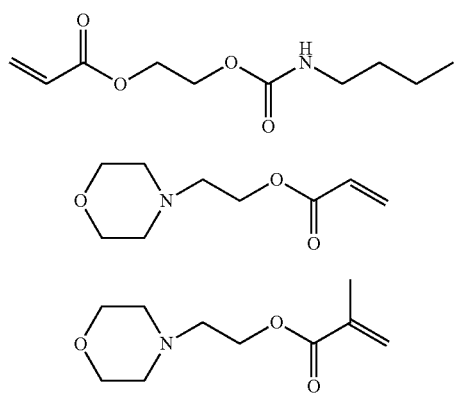

Examples 1 to 12, Comparative Examples 1 to 7

Inks for evaluation were each prepared by mixing 950 mg of the monomer compound presented in a respective column of each Example or Comparative Example in Table 1 with 50 mg of 2-methyl-1-[4-(methylthio)phenyl]-2-morpholinopropan-1-one (IRGACURE 907, manufactured by BASF Japan Ltd.) serving as a polymerization initiator, by means of a magnetic stirrer.

These inks were each evaluated in terms of photopolymerization reactivity, photocuring ability, and odor in the following manners. The results are presented in Table 1.

<Evaluation of Photopolymerization Reactivity>

An evaluation test for photopolymerization reactivity was performed on each ink using a measuring device combining DSC-7020 manufactured by Seiko Instruments Inc. with a spot light source (LA-410UV) manufactured by HAYASHI WATCH-WORKS CO., LTD. (referred to as Photo-DSC hereinafter). As for the light for radiation, light having wavelength of 365 nm was used, and the light quantity was set to 200 mW/cm$^2$.

The calorific value of the polymerization reaction carried out after radiation of light was measured by Photo-DSC. A measurement of the calorific value, which was obtained when light was applied for sufficient time to complete a polymerization reaction of the monomer compound, was performed twice on one sample. The calorific value obtained with the first measurement contains the calorific value from radiation of light as well as the calorific value from the polymerization reaction of the monomer compound. Therefore, the sample which completed the polymerization reaction by the first measurement was subjected to radiation of light under the same condition, and the calorific value of the heat other than the heat generated from the polymerization reaction of the monomer compound was measured. The calorific value of the polymerization reaction of the monomer compound was determined with a difference between the calorific value obtained in the first measurement and the calorific value obtained in the second measurement.

As for the exothermic characteristic thereof, the time required to achieve the maximum calorific value from the time for starting radiation of light was determined as T1 (sec.), which was used as an index for comparing the speed of the photopolymerization reaction.

<Evaluation of Photocuring Ability>

An evaluation for curing ability from photopolymerization was performed on each ink using a measuring device combining a rheometer VAR200AD, manufactured by REO-LOGICA Instruments AB, with an LED light source (LIGHTNINGCURE LC-L1) manufactured by Hamamatsu Photonics K.K. (referred to as Photorheometer, hereinafter).

A measurement was performed in the following manner. A sample was placed in a gap of 10 μm between a pair of corm plates each having a diameter of 20 mm, and light (365 nm, 50 mW/cm$^2$) emitted from the LED light source was applied to the sample. A change in viscoelsticity caused by curing was measured, and the time when the elastic modulus (Pa) was saturated was determined as completion of curing. Based on the measurement result, the terminal point of the elastic modulus was determined, which was determined as an index of a curing level. Typically, the level of $1\times10^4$ (Pa) is a level where the sample is completely cured. Moreover, light energy (curing energy) applied until the elastic modulus was saturated was calculated by the product of light radiation intensity (here, which was 50 mW/cm$^2$) and a period (sec.) for light radiation.

<Evaluation of Odor>

Discomfort when smelling each ink was evaluated based on the following criteria.

[Evaluation Criteria]

A: No smell was sensed.

B: Slight smell was sensed but it did not give discomfort.

C: Distinct odor gave discomfort.

D: Distinct odor gave significant discomfort.

Further, an inkjet ink was prepared using 100 parts by mass of the polymerizable compound (monomer compound) of Example of the present invention, 10 parts by mass of the polymerization initiator (IRGACURE 907, manufactured by BASF Japan Ltd.), and 3 parts by mass of a colorant. As for the colorant, MICROLITH Black C-K manufactured by BASF Japan Ltd., (carbon black pigment) was used as a black pigment, and MICROLITH Blue 4G-K manufactured by BASF Japan Ltd., was used as a blue pigment. The obtained inkjet ink composition was jetted on a commercially available slide glass to form a film, and the film was cured by applying light by means of a UV lamp system LH6, manufactured by Fusion Systems Japan K.K. at 200 mW/cm$^2$. As a result that, it was confirmed that the ink was ejected without any problem, and the film was cured.

TABLE 1

| | Monomer compound | Photopolymerization reactivity (Photo DSC) T1 (sec.) | Photocuring (photorheometer) | | Odor |
|---|---|---|---|---|---|
| | | | Elastic modulus (Pa) | Curing energy (mJ/cm$^2$) | |
| Ex. 1 | B-1 (Syn. Ex. 1) | 3.2 | 9.4*10$^3$ | 520 | B |
| Ex. 2 | D-1 (Syn. Ex. 3) | 3.2 | 7.9*10$^4$ | 175 | B |
| Ex. 3 | E-1 (Syn. Ex. 5) | 4.5 | 5.0*10$^4$ | 380 | B |
| Ex. 4 | F-1 (Syn. Ex. 7) | 3.2 | 8.4*10$^4$ | 150 | B |
| Ex. 5 | B-2 (Syn. Ex. 2) | 10.9 | 8.0*10$^4$ | 1,950 | A |
| Ex. 6 | D-2 (Syn. Ex. 4) | 7.0 | 7.6*10$^4$ | 380 | A |
| Ex. 7 | E-2 (Syn. Ex. 6) | 12.0 | 9.0*10$^4$ | 840 | A |
| Ex. 8 | F-2 (Syn. Ex. 8) | 7.0 | 9.4*10$^4$ | 430 | A |

TABLE 1-continued

| | Monomer compound | Photo-polymerization reactivity (Photo DSC) T1 (sec.) | Photocuring (photorheometer) Elastic modulus (Pa) | Photocuring (photorheometer) Curing energy (mJ/cm²) | Odor |
|---|---|---|---|---|---|
| Ex. 9 | G-3 (Syn. Ex. 9) | 2.4 | $1.0*10^5$ | 140 | A |
| Ex. 10 | J-3 (Syn. Ex. 11) | 2.4 | $1.0*10^5$ | 100 | A |
| Ex. 11 | G-4 (Syn. Ex. 10) | 4.8 | $1.0*10^5$ | 210 | A |
| Ex. 12 | J-4 (Syn. Ex. 12) | 3.0 | $1.0*10^5$ | 110 | A |
| Comp. Ex. 1 | Commercial product (a) | 2.5 | $4.8*10^4$ | 200 | D |
| Comp. Ex. 2 | Commercial product (c) | 2.5 | $3.2*10^4$ | 210 | C |
| Comp. Ex. 3 | Commercial product (d) | 4.5 | $1.3*10^4$ | 365 | C |
| Comp. Ex. 4 | Ref. Syn. Ex. 1 | 2.5 | $1.1*10^3$ (not cured) | — | D |
| Comp. Ex. 5 | Commercial product (b) | 19.3 | $8.0*10^4$ | 2,020 | D |
| Comp. Ex. 6 | Commercial product (e) | 30.3 | $8.6*10^4$ | 2,050 | C |
| Comp. Ex. 7 | Ref. Syn. Ex. 2 | 10.3 | <1.0 (not cured) | — | D |

As seen from Table 1, the inks of Examples 1 to 12 had high photopolymerization reactivity and high curing ability and had no problem of odor, and therefore these ink were excellent in practicality. The inks of Examples 1 to 4, and 9 to 10, each of which used an acrylic acid ester derivative, had small values of T1, which was an index for photoreactivity, and exhibited a fast progress of the polymerization reaction, and moreover had small curing energy in the evaluation for curing ability. Therefore, these inks were excellent in functions as a curing ink. Specially, the inks of Examples 9 to 10 were excellent.

On the other hand, the inks of Examples 5 to 8, each of which used a methacrylic acid derivative, had the larger value of T1, which was an index for photopolymerization reactivity, and lager curing energy in the evaluation for curing ability, compared to the inks of Examples 1 to 4, each of which used an acrylic acid ester derivative having the same backbone structure. However, excluding the inks of Examples 2 and 6, the elastic modulus thereof in the photocuring evaluation was high, a hard and solid cured state could be formed.

Moreover, the inks of Examples 11 to 12, each of which used a bifunctional methacrylic ester derivative, had the lager value of T1, which was an index for photopolymerization reactivity, and lager curing energy in the photocuring evaluation, compared to the inks of Examples 9 to 10, each of which used an acrylic ester derivative having the same backbone structure. However, both inks had high reactivity and curing ability. The elastic modulus of each of the cured inks of Examples 9 to 12 was high, i.e., $1.0 \times 10^5$, and these inks could form a hard and solid cured state.

Further, the inks of Examples 5 to 12 were in the level of odor evaluation where no odor was sensed, and therefore these inks had a large merit on handling as no discomfort was given.

Studying the results of Comparative Examples comparing to those of Examples, all the inks of Comparative Examples 1 to 7 had unpleasant odor. Therefore, these inks are not suitable for practical use in view of handling of the ink. For example, the inks of Comparative Examples 1 to 3 had excellent photopolymerization reactivity and had the small curing energy for photocuring, but it was found that these ink had odor of the level which gave discomfort. Further, the inks of Comparative Examples 4 and 7 had extremely low elastic modulus, to the extent that curing was not progressed even though a polymerization reaction was progressed by light radiation. Moreover, the inks of Comparative Examples 5 to 7, each of which used an acrylic acid ester derivative, had large curing energy, or had low elastic modulus after a polymerization reaction, and therefore did not have desirable photocuring ability.

Embodiments of the present invention are, for example, as follows:

<1> (Meth)acrylic acid ester containing:

one or more partial structures each represented by the following formula 1 in a molecule thereof, wherein the partial structure is a urethane structure which does not have a hydrogen atom directly bonded to a nitrogen atom of the following formula 1:

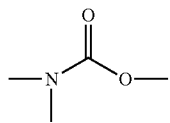

Formula 1 where the nitrogen atom is not bonded to a hydrogen atom.

<2> The (meth)acrylic acid ester according to <1>, wherein the (meth)acrylic acid ester has the structure represented by the following formula 2 or 3:

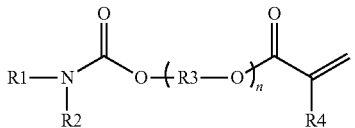

Formula 2

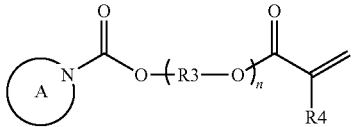

Formula 3 where R1 and R2 may be identical or different, and each represent an alkyl group or an alkyl group containing a hetero atom, R3 represents a C1-C15 bivalent group or a C1-C15 bivalent group containing a hetero atom, n represents an integer of 1 to 4, R4 represents a hydrogen atom or a methyl group, and A represents a ring structure containing at least one nitrogen atom.

<3> The (meth)acrylic acid ester according to <2>, wherein the ring structure A in the formula 3 is a morpholine ring.

<4> The (meth)acrylic acid ester according to <1>, wherein the (meth)acrylic acid ester has the structure represented by the following formula 4:

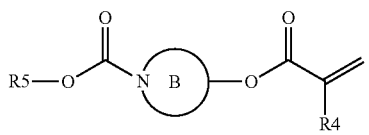

Formula 4 where R4 represents a hydrogen atom or a methyl group, R5 represents an alkyl group or an alkyl group containing a hetero atom, and B represents a ring structure containing at least one nitrogen atom.

<5> The (meth)acrylic acid ester according to <4>, wherein the ring structure B in the formula 4 is a piperidine ring.

<6> The (meth)acrylic acid ester according to any of <3> or <5>, wherein the (meth)acrylic acid ester has the structure represented by the following formula 5 or 6:

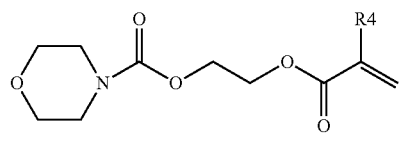

Formula 5

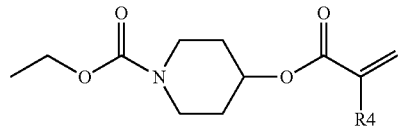

Formula 6 where R4 represents a hydrogen atom or a methyl group.

<7> The (meth)acrylic acid ester according to <1>, wherein the (meth)acrylic acid ester contains two or more partial structures each represented by the formula 1 in a molecule thereof.

<8> The (meth)acrylic acid ester according to <7>, wherein the (meth)acrylic acid ester has the structure represented by the following formula 7:

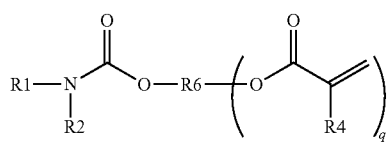

Formula 7 where R1 and R2 may be identical or different and each represents an alkyl group or an alkyl group containing a hetero atom, R6 represents a C1-C15 tri- or higher valent group or a C1-C15 tri- or higher valent group containing a hetero atom, q represents 2 or 3, and R4 represents a hydrogen atom or a methyl group, in which R1 and R2 may form a ring structure bonded via a carbon atom or a hetero atom.

<9> The (meth)acrylic acid ester according to <8>, wherein R6 in the formula 7 is a trivalent group represented by the following formula 8 or 9:

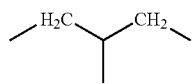

Formula 8

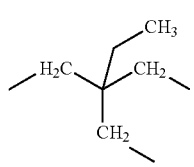

Formula 9

<10> The (meth)acrylic acid ester according to <9>, wherein the (meth)acrylic acid ester has the structure represented by the following formula 10 or 11:

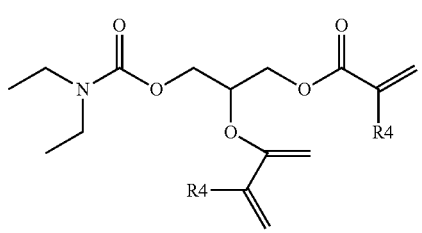

Formula 10

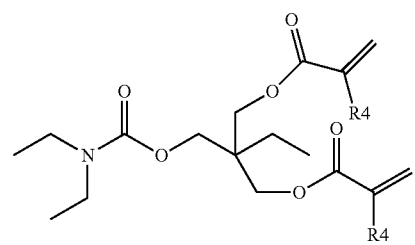

Formula 11 where R4 represents a hydrogen atom or a methyl group.

<11> An activation energy ray curing composition, containing:

the (meth)acrylic acid ester as defined in any one of <1> to <10>.

<12> An inkjet recording ink containing:

the activation energy ray curing composition as defined in <11>.

This application claims priority to Japanese application No. 2011-266160, filed on Dec. 5, 2011 and Japanese application No. 2012-110837, filed on May 14, 2012, and incorporated herein by reference.

What is claimed is:

1. An activation energy ray curing composition, comprising:
   a (meth)acrylic acid ester, and
   a photopolymerization initiator selected from the group consisting of bis(2,4,6-trimethylbenzoyl)phenyl phosphine oxide; 2,4,6-trimethylbenzoyldiphenyl phosphine oxide; 1-hydroxycyclohexylphenyl ketone; 2-methyl-1-[4-(methylthio)phenyl]-2-morpholinopropan-1-one; and 2-dimethylamino-2-(4-methylbenzyl)-1-(4-morpholin-4-yl-phenyl)butan-1-one;

wherein the (meth)acrylic acid ester is a compound of formula F-1:

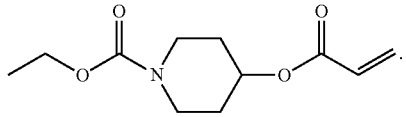

F-1

2. An inkjet recording ink comprising:

an activation energy ray curing composition, wherein the activation energy ray curing composition contains a (meth)acrylic acid ester, and a photopolymerization initiator selected from the group consisting of bis (2,4,6-trimethylbenzoyl)phenyl phosphine oxide; 2,4,6-trimethylbenzoyldiphenyl phosphine oxide; 1-hydroxycyclohexylphenyl ketone; 2-methyl-1-[4-(methylthio)phenyl]-2-morpholinopropan-1-one; and 2-dimethylamino-2-(4-methylbenzyl)-1-(4-morpholin-4-yl-phenyl)butan-1-one;

wherein the (meth)acrylic acid ester is a compound of formula F-1:

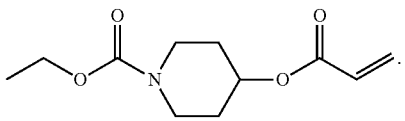

F-1

3. The inkjet recording ink of claim 2, wherein the inkjet recording ink has a viscosity of from 7 mPa·s to 30 mPa·s, under conditions at time of ejecting from an inkjet device.

4. The inkjet recording ink of claim 2, wherein the inkjet recording ink contains no solvent.

* * * * *